US012268748B2

(12) United States Patent
Shih et al.

(10) Patent No.: US 12,268,748 B2
(45) Date of Patent: Apr. 8, 2025

(54) NUCLEIC ACID NANOSTRUCTURES CROSSLINKED WITH OLIGOLYSINE

(71) Applicants: President and Fellows of Harvard College, Cambridge, MA (US); Dana-Farber Cancer Institute, Inc., Boston, MA (US)

(72) Inventors: William M. Shih, Cambridge, MA (US); Zhao Zhao, Cambridge, MA (US); Frances M. Anastassacos, Cambridge, MA (US)

(73) Assignees: President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 849 days.

(21) Appl. No.: 17/602,740

(22) PCT Filed: Apr. 9, 2020

(86) PCT No.: PCT/US2020/027435
§ 371 (c)(1),
(2) Date: Oct. 8, 2021

(87) PCT Pub. No.: WO2020/210468
PCT Pub. Date: Oct. 15, 2020

(65) Prior Publication Data
US 2022/0160885 A1 May 26, 2022

Related U.S. Application Data

(60) Provisional application No. 62/831,858, filed on Apr. 10, 2019.

(51) Int. Cl.
*A61K 47/60* (2017.01)
*A61K 47/69* (2017.01)
*C12Q 1/68* (2018.01)

(52) U.S. Cl.
CPC .......... *A61K 47/60* (2017.08); *A61K 47/6929* (2017.08)

(58) Field of Classification Search
None
See application file for complete search history.

(56) References Cited

U.S. PATENT DOCUMENTS

| | | | |
|---|---|---|---|
| 7,842,793 | B2 | 11/2010 | Rothemund |
| 8,501,923 | B2 | 8/2013 | Rothemund |
| 9,717,685 | B2 | 8/2017 | Shih et al. |
| 2005/0112578 | A1 | 5/2005 | Matsuura et al. |
| 2006/0105049 | A1 | 5/2006 | Fernandes et al. |
| 2009/0088372 | A1 | 4/2009 | Roy et al. |
| 2010/0216978 | A1 | 8/2010 | Shih |
| 2010/0324124 | A1 | 12/2010 | Irvine et al. |
| 2011/0275702 | A1 | 11/2011 | Chang et al. |
| 2011/0321183 | A1 | 12/2011 | Ploegh et al. |
| 2012/0282670 | A1 | 11/2012 | Rossomando |
| 2013/0230570 | A1 | 9/2013 | Trogler et al. |
| 2015/0064233 | A1 | 3/2015 | Shih et al. |
| 2016/0083484 | A1 | 3/2016 | Korenesvski et al. |
| 2016/0271268 | A1 | 9/2016 | Shih et al. |
| 2016/0279257 | A1 | 9/2016 | Koussa et al. |
| 2019/0083522 | A1 | 3/2019 | Shih et al. |

FOREIGN PATENT DOCUMENTS

| | | |
|---|---|---|
| CN | 101766820 B | 7/2012 |
| EP | 2275085 A1 | 1/2011 |
| JP | 2002-114797 A | 4/2002 |
| JP | 2003-522524 A | 7/2003 |
| JP | 2008-504846 A | 2/2008 |
| JP | 2008-523061 A | 7/2008 |
| JP | 2009-518008 A | 5/2009 |
| JP | 2009-213390 A | 9/2009 |
| JP | 2012-509983 A | 4/2012 |
| WO | WO 2001/18015 A1 | 3/2001 |
| WO | WO 2012/142659 A1 | 10/2012 |
| WO | WO 2013/003555 A1 | 1/2013 |
| WO | WO 2013/054286 A1 | 4/2013 |
| WO | WO 2013/113325 A1 | 8/2013 |
| WO | WO 2013/148186 A1 | 10/2013 |

OTHER PUBLICATIONS

Bikram et al., Macromolecules, vol. 37:1903-1916, 2004.*
Agarwal et al., Agnew. Chem. Int. Ed. vol. 56:5460-5464, 2017.*
International Search Report and Written Opinion mailed Jul. 18, 2013 for Application No. PCT/US2013/030765.
International Preliminary Report on Patentability mailed Oct. 9, 2014 for Application No. PCT/US2013/030765.
International Search Report and Written Opinion mailed Nov. 4, 2014 for Application No. PCT/US2014/046251.
International Preliminary Report on Patentability mailed Jan. 21, 2016 for Application No. PCT/US2014/046251.
International Search Report and Written Opinion mailed Feb. 13, 2015 for Application No. PCT/US2014/064659.
International Preliminary Report on Patentability for PCT/US2014/064659 mailed May 19, 2016.
Partial Supplementary European Search Report mailed Jul. 10, 2017 for EP 14860290.7.
Extended European Search Report mailed Oct. 18, 2017 for EP 14860290.7.
International Search Report and Written Opinion mailed Jul. 17, 2020 for Application No. PCT/US2020/027435.
International Preliminary Report on Patentability for PCT/US2020/027435 mailed Oct. 21, 2021.
Anastassacos et al., Glutaraldehyde cross-linking of oligolysines coating DNA origami greatly reduces susceptibility to nuclease degradation. J Am Chem Soc. Feb. 19, 2020;142(7):3311-3315. Epub Feb. 11, 2020.
Babic et al. Poly L-lysine-modified iron oxide nanoparticle for stem cell labelling. Bioconjug Chem. 2008;19:740-50. Epub Feb. 21, 2008.

(Continued)

*Primary Examiner* — Sean McGarry
(74) *Attorney, Agent, or Firm* — Wolf, Greenfield & Sacks, P.C.

(57) ABSTRACT

The present disclosure provides, in some aspects, nucleic acid nanostructures covalently linked to oligolysine-PEG copolymers.

20 Claims, 7 Drawing Sheets

(56) References Cited

OTHER PUBLICATIONS

Banchelli et al., Phospholipid membranes decorated by cholesterol-based oligonucleotides as soft hybrid nanostructures. J Phys Chem B. Sep. 4, 2008;112(35):10942-52.
Bellot et al., Recovery of intact DNA nanostructures after agarose gel-based separation. Nat Methods. Mar. 2011;8(3):192-4.
Bikram et al., Biodegradable Poly(ethylene glycol)-co-poly(l-lysine)-g-histidine Multiblock Copolymers for Nonviral Gene Delivery. Macromolecules. Feb. 11, 2004;37(5):1903-16.
Cecconi et al., Protein-DNA chimeras for single molecule mechanical folding studies with the optical tweezers. Eur Biophys J. Jul. 2008;37(6):729-38. doi: 10.1007/s00249-007-0247-y. Epub Jan. 9, 2008.
Chen et al., A general strategy for the evolution of bond-forming enzymes using yeast display.Proc Natl Acad Sci U S A. Jul. 12, 2011;108(28):11399-404. doi: 10.1073/pnas.1101046108. Epub Jun. 22, 2011.
Davis et al., Preparation and analysis of PEGylated poly-L-lysine DNA nanoparticles for gene delivery. Cold Spring Harb Protoc. May 2010;2010(5):pdb.prot5419. doi: 10.1101/pdb.prot5419.
Dietz et al., Folding DNA into twisted and curved nanoscale shapes. Science. Aug. 7, 2009;325(5941):725-30.
Douglas et al., Rapid prototyping of 3D DNA-origami shapes with caDNAno. Nucleic Acids Res. Aug. 2009;37(15):5001-6.
Douglas et al., Self-assembly of DNA into nanoscale three-dimensional shapes. Nature. May 21, 2009;459(7245):414-8.
Eskelinen et al., Controlling the formation of DNA origami structures with external signals. Small. Jul. 9, 2012;8(13):2016-20. doi: 10.1002/smll.201102697. Epub Apr. 17, 2012.
Evett et al., DNA-polylysine interaction as studied by polarization of fluorescence. Ann N Y Acad Sci. May 16, 1969;158(1):210-22.
Fujigaya et al., Enhanced cell uptake via non-covalent decollation of a single-walled carbon nanotube-DNA hybrid with polyethylene glycol-grafted poly(l-lysine) labeled with an Alexa-dye and its efficient uptake in a cancer cell. Nanoscale. Oct. 5, 2011;3(10):4352-8. doi: 10.1039/c1nr10635j. Epub Sep. 20, 2011.
Gordon et al., Reactivity of biarylazacyclooctynones in copper-free click chemistry. J Am Chem Soc. Jun. 6, 2012;134(22):9199-208. doi: 10.1021/ja3000936. Epub May 24, 2012.
Halvorsen et al., Nanoengineering a single-molecule mechanical switch using DNA self-assembly. Nanotechnology. Dec. 9, 2011;22(49):494005. doi: 10.1088/0957-4484/22/49/494005. Epub Nov. 21, 2011.
Han et al., DNA origami with complex curvatures in three-dimensional space. Science. Apr. 15, 2011;332(6027):342-6. doi: 10.1126/science.1202998.
HÖgberg et al., Folding DNA origami from a double-stranded source of scaffold. J Am Chem Soc. Jul. 8, 2009;131(26):9154-5. doi: 10.1021/ja902569x.
Hook et al., Supported lipid bilayers, tethered lipid vesicles, and vesicle fusion investigated using gravimetric, plasmonic, and microscopy techniques. Biointerphases. Jun. 2008;3(2):FA108.
Howarth et al., A monovalent streptavidin with a single femtomolar biotin binding site. Nat Methods. Apr. 2006;3(4):267-73.
Jones et al., Nanomaterials. Programmable materials and the nature of the DNA bond. Science. Feb. 20, 2015;347(6224):1260901. doi:10.1126/science.1260901.
Jungmann et al., Isothermal assembly of DNA origami structures using denaturing agents. J Am Chem Soc. Aug. 6, 2008;130(31):10062-3.
Kadlecova et al., DNA delivery with hyperbranched polylysine: a comparative study with linear and dendritic polylysine. J Control Release. Aug. 10, 2013;169(3):276-88. doi: 10.1016/j.jconrel.2013.01.019. Epub Feb. 1, 2013.
Kadlecova et al., Hyperbranched polylysine: a versatile, biodegradable transfection agent for the production of recombinant proteins by transient gene expression and the transfection of primary cells. Macromol Biosci. Jun. 2012; 12(6):794-804. doi: 10.1002/mabi.201100519. Epub Apr. 11, 2012.
Kazmierczak et al., Cadherin 23 and protocadherin 15 interact to form tip-link filaments in sensory hair cells. Nature. Sep. 6, 2007;449(7158):87-91.
Ke et al., Multilayer DNA origami packed on a square lattice. J Am Chem Soc. Nov. 4, 2009;131(43):15903-8. doi: 10.1021/ja906381y.
Ko et al., Self-assembling micelle-like nanoparticles based on phospholipid-polyethyleneimine conjugates for systemic gene delivery. J Control Release. Jan. 19, 2009;133(2):132-8.
Kwoh et al., Stablilization of poly-L-lysine/DNA polyplexes for in vivo gene delivery to the liver. Biochimica et Biophysica Acta. 1999; 1444:171-90.
Langecker et al., Synthetic lipid membrane channels formed by designed DNA nanostructures. Science. Nov. 16, 2012;338(6109):932-6. doi: 10.1126/science.1225624.
Liedl et al., Self-assembly of three-dimensional prestressed tensegrity structures from DNA. Nat Nanotechnol. Jul. 2010;5(7):520-4. doi: 10.1038/nnano.2010.107. Epub Jun. 20, 2010.
Linko et al., The enabled state of DNA nanotechnology. Curr Opin Biotechnol. Aug. 2013;24(4):555-61. doi: 10.1016/j.copbio.2013.02.001. Epub Apr. 6, 2013.
Liu et al., Biological properties of poly-L-lysine-DNA complexes generated by cooperative binding of the polycation. J Biol Chem. Sep. 14, 2001;276(37):34379-87. Epub Jul. 3, 2001.
Mann et al., DNA condensation by poly-L-lysine at the single molecule level: role of DNA concentration and polymer length. J Control Release. Feb. 11, 2008;125(3):252-62. Epub Nov. 1, 2007.
Martin, Functional Synthetic DNA Nanostructures. Dissertation. Technische Universität München, Laboratory for Biomolecular Nanotechnology. Filed on Mar. 12, 2013.
Maruyama et al., Characterization of interpolyelectrolyte complexes between double- stranded DNA and polylysine comb-type copolymers having hydrophilic side chains. Bioconjugate Chem. 1998;9:292-9. Epub Feb. 24, 1998.
Molas et al., Single-stranded DNA condensed with poly-L-lysine results in nanometric particles that are significantly smaller, more stable in physiological ionic strength fluids and afford higher efficiency of gene delivery than their double-stranded counterparts. Biochim Biophys Acta. Aug. 15, 2002;1572(1):37-44.
Niemeyer, The developments of semisynthetic DNA-protein conjugates. Trends Biotechnol. Sep. 2002;20(9):395-401.
Nikolov et al., Behavior of giant vesicles with anchored DNA molecules. Biophys J. Jun. 15, 2007;92(12):4356-68.
Pinheiro et al., Challenges and opportunities for structural DNA nanotechnology. Nat Nanotechnol. Nov. 6, 2011;6(12):763-72.
Ponnuswamy et al., Oligolysine-based coating protects DNA nanostructures from low-salt denaturation and nuclease degradation. Nat Commun. May 31, 2017;8:15654(1-9).
Ponnuswamy, Polymine induced stability of DNA nanostructures against Mg depletion and nuclease activity. Presentation. Dana Farber Institute. Wyss Institute. Oct. 17, 2013.
Popp et al., Sortagging: a versatile method for protein labeling.Nat Chem Biol. Nov. 2007;3(11):707-8. Epub Sep. 23, 2007.
Rothemund, Folding DNA to create nanoscale shapes and patterns. Nature. Mar. 16, 2006;440(7082):297-302.
Sacca et al., Functionalization of DNA nanostructures with proteins. Chem Soc Rev. Dec. 2011;40(12):5910-21. doi: 10.1039/c1cs15212b. Epub Oct. 5, 2011.
Schaeffer et al., Synthesis and applications of covalent protein-DNA conjugates. Aust J Chem. Jan. 1, 2009;62(10):1328-1332.
Shih et al., A 1.7-kilobase single-stranded DNA that folds into a nanoscale octahedron. Nature. Feb. 12, 2004;427(6975):618-21.
Shih et al., Biomolecular assembly: dynamic DNA. Nat Mater. Feb. 2008;7(2):98-100.
Shih et al., Knitting complex weaves with DNA origami. Curr Opin Struct Biol. Jun. 2010;20(3):276-82. doi: 10.1016/j.sbi.2010.03.009. Epub Apr. 22, 2010.
Shih et al., poster. DNA-Based Molecular Containers and NMR Alignment Media. 2006. 1 page.
Sotomayor et al., Structural determinants of cadherin-23 function in hearing and deafness. Neuron. Apr. 15, 2010;66(1):85-100. doi: 10.1016/j.neuron.2010.03.028.

(56) References Cited

OTHER PUBLICATIONS

Sotomayor et al., Structure of a force-conveying cadherin bond essential for inner-ear mechanotransduction. Nature. Dec. 6, 2012;492(7427):128-32. doi: 10.1038/nature11590. Epub Nov. 7, 2012.

Walsh et al., DNA cage delivery to mammalian cells. ACS Nano. 2011;5(7):5427-32. Epub Jun. 22, 2011. Supplemental information, 12 pages.

Yang et al., Nanostructures as Programmable Biomolecular Scaffolds. Bioconjug Chem. Aug. 19, 2015;26(8):1381-95. doi:10.1021/acs.bioconjchem.5b00194. Epub May 22, 2015.

Yoshina-Ishii et al., General method for modification of liposomes for encoded assembly on supported bilayers. J Am Chem Soc. Feb. 9, 2005;127(5):1356-7.

Zama et al., The study of the DNA structure in DNA-polylysine and DNA-polyarginine complexes: induced optical activities of bound dyes.Biochim Biophys Acta. Jan. 19, 1973;294(1):214-26.

Zhang et al., Structural DNA nanotechnology: state of the art and future perspective. J Am Chem Soc. Aug. 13, 2014;136(32):11198-211. doi:10.1021/ja505101a. Epub Jul. 28, 2014.

Zhou et al., Lipophilic polylysines mediate efficient DNA transfection in mammalian cells. Biochim Biophys Acta. May 31, 1991;1065(1):8-14.

Zhu et al., A novel nonviral nanoparticle gene vector: Poly-L-lysine-silica nanoparticles. Chinese Science Bulletin. Apr. 2002, 47(8): 654-658.

* cited by examiner

NUCLEIC ACID NANOSTRUCTURES CROSSLINKED WITH OLIGOLYSINE

RELATED APPLICATIONS

This application is a national stage filing under 32 U.S.C. § 371 of international application number PCT/US2020/027435, filed Apr. 9, 2020, which claims the benefit under 35 U.S.C. § 119(e) of U.S. provisional application No. 62/831,858, filed Apr. 10, 2019, the entire contents of each of which are incorporated herein by reference.

FEDERALLY SPONSORED RESEARCH

This invention was made with Government support under GM131401 awarded by the National Institutes of Health. The Government has certain rights in the invention.

BACKGROUND

DNA nanostructures (DNs) have garnered a large amount of interest as a potential therapeutic modality. These biodegradable nanoparticles are easily programmable into precise geometric configurations, can be functionalized to display a range of biological agents on their surface, and can display reactive and "smart" capabilities. DNA nanostructures, however, are prone to nuclease-mediated degradation and tend to be unstable in low Mg2+ conditions, which greatly limits their utility in physiological settings, for example as therapeutics or therapeutic delivery vehicles.

SUMMARY

Provided herein, in some aspects, are DNA nanostructures (DNs) comprising (e.g., coated with) an oligolysine-PEG copolymer that has undergone a crosslinking reaction using, for example, glutaraldehyde to improve the lifespan of DNA nanostructures >10,000-fold under strenuous nuclease, low-salt conditions compared to uncoated DNs. This provides an off-the-shelf and generalizable method for protecting DNs for in vivo applications. Further, these stabilized "cross-linked and coated DNs" (ccDNs), based on in vitro data using mammalian cells, are expected to have improved cellular uptake and bioavailability in vivo.

DNs are highly biocompatible and have unique advantages that render them attractive candidates for therapeutics or diagnostic applications. DNs can be programmed and folded into a great diversity of spatial conformations and their surfaces can be functionalized with different guests with nanoscale precision. Further, reactive capabilities to—e.g. pH or presence of biomolecules—can be engineered into certain DNs making them responsive to exposure to different biological settings.

The folding of DNs requires bringing DNA helices and thus their negatively charged backbones into close proximity. This is thermodynamically unfavorable and requires high concentrations of divalent cations (most commonly, $Mg^{2+}$) to screen the electrostatic repulsion between anionic phosphate backbones. Typically, concentrations between 6-16 mM $MgCl_2$ are included in folding DNs, though the exact concentration is structure-dependent. In most physiological buffers, $[Mg^{2+}]<0.5$ mM. DNs are prone to denaturation under low $[Mg^{2+}]$ conditions such as those found in physiological buffers and in vivo.

The application of DNs in vivo are also challenged by DNs inherent susceptibility to nuclease-mediated degradation. DNase I and DNase II are the most common nucleases in human blood and serum. In freshly prepared RPMI medium with 10% FBS, the half-life of DNs is ~12 min (Ponnuswamy N. et al. *Nature Communications* 8(15654), 2017, incorporated herein by reference). Further, clearance rate of intravenous injection of fluorescently labelled DNs is similar to that of control oligonucleotides. DNs are therefore prone to rapid degradation by nucleases in vivo.

DNs should first be stabilized against low $Mg^{2+}$-based denaturation and nuclease degradation before they can used in biomedical applications. Ideally, the structural integrity of the DNs used as therapeutic nanoparticles should be maintained for more than 24 hours. Further, they often require specialized design considerations and cannot be applied to different structures without substantial optimization. Recent data has shown that protective coating method using an oligolysine-PEG5K copolymer which when applied to DNs afforded a 100-fold increase in half-life in media supplemented with 10% FBS (~36 hours). Further, this reduced clearance and extended biological half-life from ~5 min for bare DNs to ~45 min for oligolysine-PEG5K coated DNs. While this technique shows an improvement in survivability, it does not extend the lifetime of DNs to the standards required by most biomedical applications.

The data provided herein shows unexpectedly that application of an oligolysine-PEG5K copolymer coating followed by covalent crosslinking of the copolymer using glutaraldehyde, which was previously thought to be inefficient for modifying DNA particularly at moderate temperatures, extends the half-life of DNs under strenuous DNase I conditions (1 U/µL DNase I) by 10,000× compared to bare DNs and at least ~180-fold compared to oligolysine-PEG5K coated DNs without crosslinking. This method is inexpensive, scalable and is generally applicable to a diverse range of DNs.

Thus, some aspects of the present disclosure provide a DNA nanostructure comprising (e.g., coated with) and covalently crosslinked with oligolysine-polyethylene glycol (PEG) copolymer.

In some embodiments, the DNA nanostructure and copolymer has an N:P (nitrogen in lysine to phosphorus in nucleic acid) ratio of 0.1:1 to 1:1 (e.g., 0.2:1, 0.3:1, 0.4:1, 0.5:1, 0.6:1, 0.7:1, 0.8:1, 0.9:1, or 1:1).

In some embodiments, primary amines of the DNA nanostructure form amine or imine bonds with the oligolysine-PEG copolymer.

In some embodiments, the DNA nanostructure has a half-life that is at least 100-fold, at least 1000-fold, or at least 10000-fold greater than the half-life of an uncoated (bare) DNA nanostructure.

In some embodiments, the DNA nanostructure has a half-life that is at least 150-fold, at least 160-fold, at least 170-fold, at least 180-fold, at least 190-fold, or least 200-fold greater than the half-life of a DNA nanostructure comprising (e.g., coated with) but not crosslinked with oligolysine-PEG copolymer.

In some embodiments, the DNA nanostructure maintains structural stability for at least 24 hours, at least 48 hours, or at least 72 hours in a physiological buffer comprising less than 10 mM, less than 5 mM, less than 1 mM, or less than 0.5 mM $Mg^{2+}$.

In some embodiments, the DNA nanostructure is a three-dimensional DNA nanostructure. In some embodiments, the DNA nanostructure has a void volume (uncondensed, open space) of at least 25%, at least 50%, or at least 75%.

In some embodiments, the oligolysine-PEG copolymer comprises 5 to 20 lysines (lysine amino acid residues), or 5 to 10 lysines. In some embodiments, the oligolysine-PEG copolymer comprises at least 5 lysines, at least 10 lysines, at least 15 lysines, or at least 20 lysines.

In some embodiments, the PEG is PEG1K ($M_n$ 1000), PEG5K ($M_n$ 5000), PEG10K ($M_n$ 10000), or PEG20K ($M_n$ 20000). In some embodiments, the PEG is PEG-5K.

Some aspects of the present disclosure provide compositions comprising a physiological buffer comprising less than 0.5 mM $Mg^{2+}$ and a DNA nanostructure comprising (e.g., coated with) and covalently crosslinked with oligolysine-PEG copolymer (e.g., at a N:P (nitrogen in lysine to phosphorus in nucleic acid) ratio of 0.1:1 to 1:1).

In some embodiments, the compositions further comprise DNase I, optionally at a concentration of 300-1000 U/L (e.g., 300-400 U/L).

Other aspects of the present disclosure provide methods comprising administering to a subject a DNA nanostructure comprising (e.g., coated with) and covalently crosslinked with oligolysine-PEG copolymer, as described herein. In some embodiments, the subject is a human subject. In some embodiments, the DNA nanostructure is administered subcutaneously or intravenously.

Still other aspects provide methods that comprise delivering to cells a DNA nanostructure comprising (e.g., coated with) and covalently crosslinked with oligolysine-PEG copolymer.

Further aspects provide methods that comprise coating a DNA nanostructure with oligolysine-PEG copolymer, and crosslinking the oligolysine-PEG copolymer to the DNA nanostructure using glutaraldehyde to form imine bonds with primary amines in the oligolysine-PEG copolymer. In some embodiments, the methods further comprise reducing the imine bonds to amine bonds using a reducing agent, optionally wherein the reducing agent is sodium borohydride.

Also provided herein are methods of producing a DNA nanostructure comprising (e.g., coated with) and covalently crosslinked oligolysine-PEG, the method comprising: (i) adding oligolysine-PEG to a solution comprising a DNA nanostructure; (ii) adding a crosslinking agent to the solution of (i); and (iii) adding a reducing agent to the solution of (ii) to produce a three-dimensional nucleic acid nanostructure comprising (e.g., coated with) and covalently crosslinked oligolysine-PEG.

It should be understood that the term "oligolysine" herein encompasses oligolysine homopolymers and oligolysine copolymers (e.g., comprising oligolysine and PEG, such as PEG5K).

It should also be understood that the nucleic acid (e.g., DNA) nanostructures provided herein that are covalently linked (crosslinked) to oligolysine-PEG copolymers are considered to be "coated with" the oligolysine-PEG copolymers and have, for example, an N:P ratio of about 1:1.

Anastassacos F M et al. *J. Am. Chem. Soc.* 2020, 142, 3311-3315 is herein incorporated by reference in its entirety.

BRIEF DESCRIPTION OF DRAWINGS

(FIG. 6C) TEM images show surviving intact XK10P-DNs after incubation with 1 U/μL DNase I at 37° C. over 7 and 14 days (=168 and 336 h, respectively). Scale bars, 100 nm.

DETAILED DESCRIPTION OF INVENTION

Figures 1A, 1B, 1C, 1D, 1E, 1F, 1G:
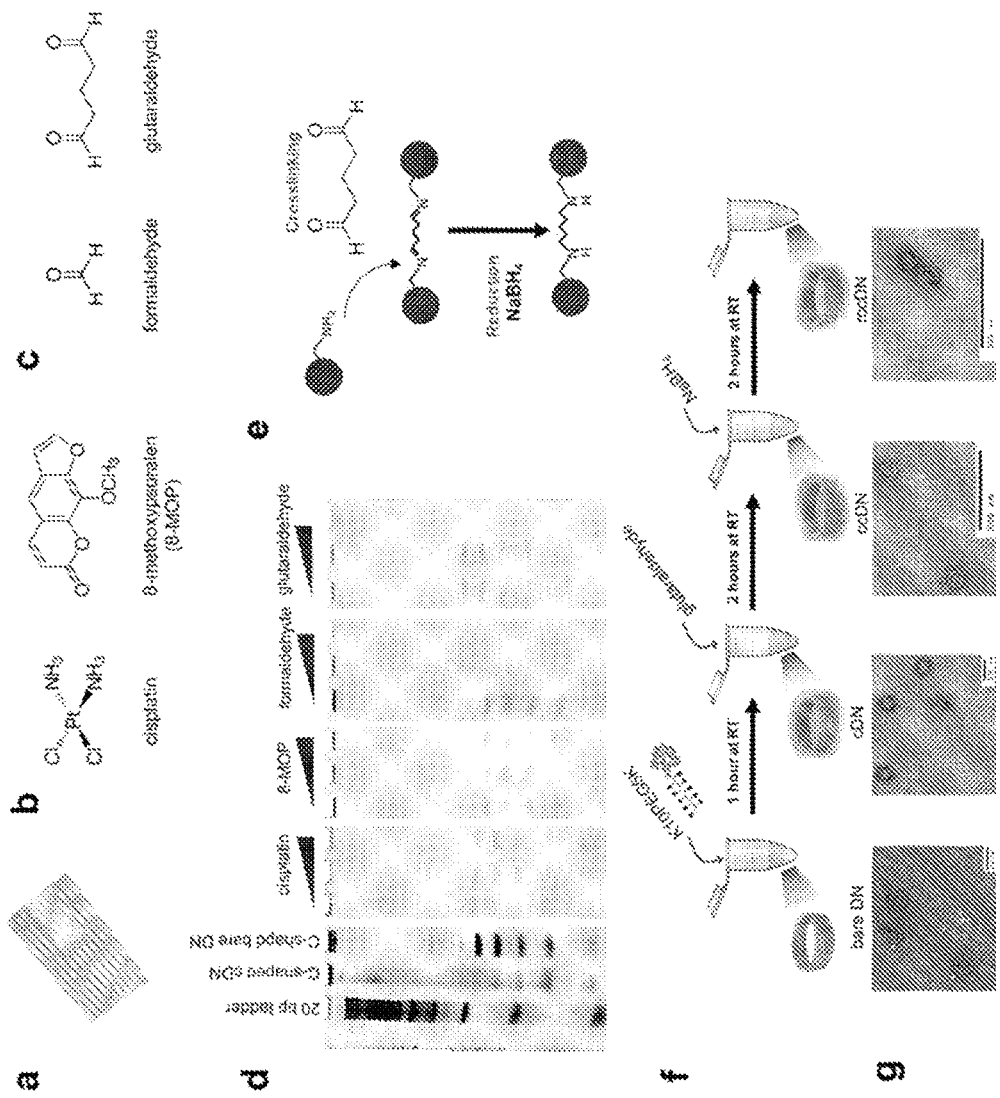
FIG. 1A shows a graphical rendering of a "C-shaped" nucleic acid nanostructure.
FIG. 1B provides exemplary nucleic acid crosslinking agents.
FIG. 1C provides exemplary aldehyde crosslinking agents.
FIG. 1D shows a denaturing polyacrylamide gel electrophoresis (PAGE) assay involving increasing concentrations of crosslinking agents incubated with "C-shaped" nucleic acid nanostructure comprising (e.g., coated with) a polylysine polymer ($K_{10}$-PEG5K).
FIG. 1E shows a schematic of a crosslinking reaction between proximal amines with glutaraldehyde to form imine bonds followed by reduction to secondary amines by sodium borohydride ($NaBH_4$).
FIG. 1F shows a schematic of manufacturing pipeline producing a three-dimensional nucleic acid nanostructure comprising (e.g., coated with) a covalently crosslinked polylysine polymer ($K_{10}$-PEG5K).
FIG. 1G shows negative stain transmission electron microscopy (TEM) images of barrel shaped nucleic acid nanostructures—without polymer coating (bare DN), with non-covalent polymer ($K_{10}$-PEG5K) coating (cDN), with covalent polymer ($K_{10}$-PEG5K) coating (ccDN), and with covalent polymer ($K_{10}$-PEG5K) coating following reduction by sodium borohydride (rccDN).

Nucleic acids (e.g., DNA) can be fabricated as three-dimensional nanostructures that are, for example, several mega-daltons in size. One such method of DNA nanostructure fabrication is referred to as DNA origami, which includes producing three-dimensional nucleic acid structures of arbitrary, predefined shape and size (see, e.g., WO 2013148186 A1). Nucleic acid nanostructures have great potential in biomedical applications, particularly because they are biodegradable, can be functionalized in a site-specific manner, and can be engineered to undergo allosteric conformational changes, allowing for precise interactions with target molecules and cells.

Practically, however, nucleic acid nanostructures have limited uses in the biomedical field due, in part, to poor structural integrity and rapid degradation under physiological conditions. Nucleic acid nanostructures typically require up to 16 mM magnesium ion ($Mg^{2+}$) to neutralize electrostatic repulsion and thereby stabilize their shape. Thus, nucleic acid nanostructures exhibit poor structural integrity in biological buffers (e.g., buffers containing physiological levels of $Mg^{2+}$ (e.g., 0.6 mM) and $Ca^{2+}$ (e.g., 1.2 mM)). Additionally, the activity of DNase I in freshly prepared cell medium containing 10% fetal bovine serum, which is typically used in biomedical applications, causes rapid degradation of nucleic acid nanostructures.

Provided herein, in various aspects and embodiments, are nucleic acid nanostructures that are engineered to maintain their structural integrity and resist nuclease degradation, even under physiological conditions of magnesium depletion and nuclease activity. Nucleic acid nanostructures herein are typically covalently linked to (e.g., coated with) positively charged oligolysine, which neutralize electrostatic repulsion and enhance nucleic acid resistance to nuclease degradation, thereby stabilizing the shape of the nanostructures. Without being bound by any particular theory, the primary interaction between oligolysine and nucleic acid nanostructures is electrostatic: positively charged polymers can weave into the nanostructures to shield the negatively charged phosphate backbone of the nucleic acids and thus promote close packing of nucleic acid helices.

Aspects of the present disclosure provide nucleic acid nanostructures covalently linked to (e.g., coated with) oligolysine-PEG copolymer that protect the nanostructures from degradation, for example, under physiological conditions of magnesium and/or calcium depletion and nuclease activity. Nucleic acid nanostructures, in general, typically require up to 16 mM magnesium ion ($Mg2^+$) to neutralize electrostatic repulsion and thereby stabilize their shape. Thus, such structures exhibit poor structural integrity in biological buffers (e.g., buffers containing physiological levels of $Mg2^+$ (e.g., 0.6 mM) and $Ca2^+$ (e.g., 1.2 mM)). Further, the activity of DNase I in freshly prepared cell medium containing 10% fetal bovine serum, which is typically used in biomedical applications, causes rapid degradation of nucleic acid nanostructures. The structural integrity of nucleic acid nanostructures can be maintained, even under physiological conditions (e.g., including low salt conditions), by linking the nanostructures to positively charged oligolysine (e.g., oligolysine copolymer comprising lysine amino acids and PEG moieties), which neutralize electrostatic repulsion and enhance nucleic acid resistance to nuclease degradation, thereby stabilizing the shape of the nanostructures.

Nucleic acid nanostructures may be covalently linked to (e.g., coated with) oligolysine such that the covalent crosslink occurs between an oligolysine and the nucleic acid nanostructure involves the amine of a lysine amino acid side chain of the polylysine polymer. The covalent crosslink may be formed using an aldehyde crosslinking agent or any suitable crosslinking agent. In some embodiments, an aldehyde crosslinking agent is formaldehyde or glutaraldehyde.

Nucleic acid nanostructures may be covalently linked to (e.g., coated with) oligolysine such that the covalent crosslink occurs between any atom of an oligolysine and any atom of the nucleic acid nanostructure. In some embodiments, the covalent crosslink is formed using a nucleic acid crosslinking agent. In some embodiments, a nucleic acid crosslinking agent is cisplatin or methoxypsoralen (8-MOP).

Oligolysine (e.g., oligolysine copolymer comprising lysine amino acids and PEG moieties) of the present invention is a cationic polymer, which, without being bound by any particular theory, may be used to shield the negatively charged phosphate backbone of nucleic acids, thereby promoting close packing of nucleic acid helices to stabilize the shape of and slow down nuclease degradation of the nanostructures.

Oligolysine may comprise any one or more functional groups in addition to its primary amine groups. As used herein, a "functional group" refers to an atom or group of atoms, such as a carboxyl group, that replaces hydrogen in an organic compound and determines the chemical behavior of the compound. Examples of common functional groups include, without limitation, alkane, ether, ketone, alkene, aldehyde, alkyne, imine, carboxylic acid, alkyl halide, ester, alcohol, ester, thioester, thiol, amide, acyl phosphate, acid chloride, thioether, phosphate monoester, phenol, and phosphate diester. Oligolysine (e.g., oligolysine copolymer comprising lysine amino acids and PEG moieties) of the present disclosure include linear, branched and dendrimer polymers. Oligolysine (e.g., oligolysine copolymer comprising lysine amino acids and PEG moieties) of the present disclosure, in some embodiments, are not limited by length of the polymer.

The length of oligolysine (e.g., oligolysine copolymer comprising lysine amino acids and PEG moieties) may vary. In some embodiments, the length of an oligolysine is 5-100 lysines (i.e., the oligolysine comprise 5-100 lysines). For example, the length of an oligolysine may be 5-75, 5-50, 5-25, 5-20, 5-25, or 5-10 lysines. In some embodiments, the length of an oligolysine is 5, 10, 15, 20, 25, 30, 35, 40, 45, 50, 55, 60, 65, 70, 75, 80, 85, 90, 95, or 100 lysines.

In some embodiments, an oligolysine (e.g., oligolysine copolymer comprising lysine amino acids and PEG moieties) includes one or more additional amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine) and/or analogs thereof. Thus, oligolysine may comprise or consist of peptides (e.g., short chains of amino acid monomers linked by peptide (e.g., amide) bonds). In some embodiments, oligolysine comprise positively charged amino acids such as lysine and/or arginine. In some embodiments, the oligolysine may comprise poly-L-lysine polymers. In some embodiments, the oligolysine may comprise poly-L-lysine polymers and PEG moieties.

In some embodiments, an oligolysine (e.g., oligolysine copolymer comprising lysine amino acids and PEG moieties) comprises a plurality of lysines. In some embodiments, an oligolysine comprises at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% lysine amino acids. In some embodiments, a region of amino acids comprises 50% to 100%, 55% to 100%, 60% to 100%, 65% to 100%, 70% to 100%, 75% to 100%, 80% to 100%, 85% to 100% or 90% to 100% lysine amino acids.

Lysines of oligolysine (e.g., oligolysine copolymer comprising lysine amino acids and PEG moieties), in some embodiments, are separated from each other by at least 1, at least 2, at least 3, at least 4, at least 5, at least 6, at least 7, at least 8, at least 9, at least 10 or more, non-amine containing amino acids such as non-lysine amino acids. In some embodiments, lysines of oligolysine are separated from each other by 1 to 5, or 1 to 10, non-amine containing amino acids such as non-lysine amino acids. In some embodiments, lysines of oligolysine are regularly spaced. The following are non-limiting examples of linear oligolysine having regularly-spaced lysine (K), where X is a non-lysine amino acid, or functional group, and n is any integer equal to or greater than 1:

```
(i) K-X-(K-X-)_n-K,
or
X-(K-X-)_n, K-X-(K-X-)_n,
or
X-(K-X-)_n-K;

(ii) K-X-X-(K-X-X-)_n-K,
or
X-X-(K-X-X-)_n,
or
K-X-X-(K-X-X-)_n,
or
X-X-(K-X-X-)_n-K;
or (iii) K-X-X-X-(K-X-X-X-)_n-K,
or
X-X-X-(K-X-X-X)_n,
or
K-X-X-X-(K-X-X-X-)_n,
or
X-X-X-(K-X-X-X)_n-K.
```

In some embodiments, the oligolysine herein comprise a polyethylene glycol (PEG) moiety or a related ether-containing functional group. A PEG moiety may comprise at least 5, at least 10, at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1250, at least 1500, or at least 2000 polyethylene glycol monomer units. In some embodiments, a PEG moiety may comprise 5-100, 50-100, 50-200, 100-200, 100-150, 200-250, 200-300, 250-500, 400-600, 500-1000, 750-1000, 750-1500, or 1250-2000 polyethylene glycol monomer units. In some embodiments, a PEG moiety is PEG 1K (average molecular weight of 1000 Daltons), PEG 5K (average molecular weight of 5000 Daltons), PEG 10K (average molecular weight of 10000 Daltons), PEG 20K (average molecular weight of 20000 Daltons), PEG 25K (average molecular weight of 25000 Daltons), PEG 50K (average molecular weight of 50000 Daltons), or PEG 100K (average molecular weight of 100000 Daltons).

A "nucleic acid nanostructure," as used herein, refers to nucleic acids that form (e.g., self-assemble) two-dimensional (2D) or three-dimensional (3D) shapes (e.g., reviewed in W. M. Shih, C. Lin, *Curr. Opin. Struct. Biol.* 20, 276 (2010), incorporated by reference herein). Nanostructures may be formed using any nucleic acid folding or hybridization methodology. One such methodology is DNA origami (see, e.g., Rothmund, P. W. K. *Nature* 440 (7082): 297-302 (2006), incorporated by reference herein). In a DNA origami approach, a nanostructure is produced by the folding of a longer "scaffold" nucleic acid strand through its hybridization to a plurality of shorter "staple" oligonucleotides, each of which hybridize to two or more non-contiguous regions within the scaffold strand. In some embodiments, a scaffold strand is at least 100 nucleotides in length. In some embodiments, a scaffold strand is at least 500, at least 1000, at least 2000, at least 3000, at least 4000, at least 5000, at least 6000, at least 7000, or at least 8000 nucleotides in length. The scaffold strand may be naturally or non-naturally occurring. Staple strands are typically less than 100 nucleotides in length; however, they may be longer or shorter depending on the application and depending upon the length of the scaffold strand. In some embodiments, a staple strand may be 15 to 100 nucleotides in length. In some embodiments, a staple strand is 25 to 50 nucleotides in length.

In some embodiments, a nucleic acid nanostructure may be assembled in the absence of a scaffold strand (e.g., a scaffold-free structure). For example, a number of oligonucleotides (e.g., less than 200 nucleotides or less than 100 nucleotides in length) may be assembled to form a nucleic acid nanostructure.

Other methods for assembling nucleic acid nanostructures are known in the art, any one of which may be used herein. Such methods are described by, for example, Bellot G. et al., *Nature Methods,* 8: 192-194 (2011); Liedl T. et al, *Nature Nanotechnology,* 5: 520-524 (2010); Shih W. M. et al, *Curr. Opin. Struct. Biol.,* 20: 276-282 (2010); Ke Y. et al, *J. Am. Chem. Soc,* 131: 15903-08 (2009); Dietz H. et al, *Science,* 325: 725-30 (2009); Hogberg B. et al, *J. Am. Chem. Soc,* 131: 9154-55 (2009); Douglas S. M. et al, *Nature,* 459: 414-418 (2009); Jungmann R. et al, *J. Am. Chem. Soc,* 130: 10062-63 (2008); Shih W. M., *Nature Materials,* 7: 98-100 (2008); and Shih W. M., *Nature,* All: 618-21 (2004), each of which is incorporated herein by reference in its entirety.

A nucleic acid nanostructure may be assembled into one of many defined and predetermined shapes including without limitation a capsule, hemi-sphere, a cube, a cuboidal, a tetrahedron, a cylinder, a cone, an octahedron, a prism, a sphere, a pyramid, a dodecahedron, a tube, an irregular shape, and an abstract shape. The nanostructure may have a void volume (e.g., it may be partially or wholly hollow). In some embodiments, the void volume may be at least 25%, at least 50%, at least 75%, at least 85%, at least 90%, or more of the volume of the nanostructure. Thus, in some embodiments, nucleic acid nanostructures do not comprise a solid core. In some embodiments, nucleic acid nanostructures are not circular or near circular in shape. In some embodiments, nucleic acid nanostructures are not a solid core sphere. Depending on the intended use, nucleic acid nanostructures may be assembled into a shape as simple as a two-dimensional sheet or as complex as a three-dimensional capsule or lattice (or even more complex).

In some embodiments, the nucleic acid nanostructure is a nucleic acid (e.g., DNA) origami nanostructure. In some embodiments, the nucleic acid nanostructure is a nucleic acid (e.g., DNA) single-stranded tile (SST) nanostructure.

Nucleic acid nanostructures may be made of, or comprise, DNA, RNA, modified DNA, modified RNA, PNA, LNA or a combination thereof.

In some embodiments, nucleic acid nanostructures are rationally designed. A nucleic acid nanostructure is herein considered to be "rationally designed" if nucleic acids that form the nanostructure are selected based on pre-determined, predictable nucleotide base pairing interactions that direct nucleic acid hybridization. For example, nucleic acid nanostructures may be designed prior to their synthesis, and their size, shape, complexity and modification may be prescribed and controlled using certain select nucleotides (e.g., oligonucleotides) in the synthesis process. The location of each nucleic acid in the structure may be known and provided for before synthesizing a nanostructure of a particular shape. The fundamental principle for designing, for example, self-assembled nucleic acid nanostructures is that sequence complementarity in nucleic acid strands is selected such that, by pairing up complementary segments, the nucleic acid strands self-organize into a predefined nanostructure under appropriate physical conditions. Thus, in some embodiments, nucleic acid nanostructures are self-assembling. Similarly, handles and anti-handle nucleic acids (e.g., those linked to agents or targeting molecules) may be rationally designed to attach specifically to an interior or exterior surface of a nanostructure, in some embodiments, without intercalation or hybridization with nucleic acids forming the body of the nanostructure.

Examples of nucleic acid nanostructures for use in accordance with the present disclosure include, without limitation, capsules, lattices (E. Winfree, et al. *Nature* 394, 539 (1998); H. Yan, et al. *Science* 301, 1882 (2003); H. Yan, et al. *Proc. Natl. Acad. of Sci. USA* 100, 8103 (2003); D. Liu, et al. *J. Am. Chem. Soc.* 126, 2324 (2004); P. W. K. Rothemund, et al. *PLoS Biology* 2, 2041 (2004)), ribbons (S. H. Park, et al. *Nano Lett.* 5, 729 (2005); P. Yin, et al. *Science* 321, 824 (2008)), tubes (H. Yan *Science* (2003); P. Yin (2008)), finite two-dimensional (2D) and three dimensional (3D) objects with defined shapes (J. Chen, N. C. Seeman, *Nature* 350, 631 (1991); P. W. K. Rothemund, *Nature* 440, 297 (2006); Y. He, et al. *Nature* 452, 198 (2008); Y. Ke, et al. *Nano. Lett.* 9, 2445 (2009); S. M. Douglas, et al. *Nature* 459, 414 (2009); H. Dietz, et al. *Science* 325, 725 (2009); E. S. Andersen, et al. *Nature* 459, 73 (2009); T. Liedl, et al. *Nature Nanotech.* 5, 520 (2010); D. Han, et al. *Science* 332, 342 (2011)), and macroscopic crystals (J. P. Meng, et al. *Nature* 461, 74 (2009)). Other nucleic acid nanostructures may be used as provided herein.

Polylysine, a cationic polymer, is known to be efficient in condensing plasmid DNA into compact particles, for example, for delivery of therapeutic DNA. DNA is a highly negatively charged polymer due to the repeating phosphate groups along the polymer backbone. The interaction with cationic polymers such as polylysine is therefore an electrostatic one. It is generally accepted that DNA condensation occurs through neutralization of negative charges on the DNA by its interactions with cationic oligolysine, followed by hydrophobic collapse as water is displaced from the DNA structure. Generally, DNA is super-saturated with oligolysine such that most or all of the negative charges of the DNA are neutralized, and the DNA condenses into a compact particle of 12 nm to 300 nm in diameter, depending on the weight of the polylysine polymer and the condensation conditions (e.g., charge ratio between polymer and DNA, salt concentration and temperature). In some embodiments, the term "condensed nucleic acid" refers to a nucleic acid particle that has a diameter and/or volume that is less than 80%, less than 70%, less than 60%, less than 50%, or less than 40% of the diameter and/or volume of its non-condensed state (e.g., without being supersaturated with polylysine). Unlike the condensed, compacted DNA particles described above, the nucleic acid nanostructures of the present disclosure are not condensed into compact particles when complexed with oligolysine-PEG copolymers in accordance with the present disclosure. Rather, nucleic acid nanostructures provided herein maintain their structure integrity. In some embodiments, the nucleic acid nanostructures are "subsaturated" or "saturated" with covalently linked oligolysine-PEG copolymers (e.g., coated with oligolysine-PEG copolymers at a N:P (nitrogen in lysine to phosphorus in nucleic acid) ratio of 0.1:1 to 1:1) such that the architecture of the structures is not compromised. That is, nucleic acid nanostructures of the present disclosure have a 2D or 3D shape, despite the additional weight of and covalent interactions with positively-charged oligolysine.

Surprisingly, nucleic acid nanostructures that are covalently linked to oligolysine-PEG copolymers as described herein are even more structurally stable and are more resistant to degradation (e.g., at low and/or physiological salt concentrations, in presence of nucleases) than nanostructures that are non-covalently linked to oligolysine. In some embodiments, nucleic acid nanostructures that are covalently linked to oligolysine-PEG copolymers are at least 2-fold, at least 5-fold, at least 10-fold, at least 20-fold, at least 50-fold, at least 100-fold, at least 150-fold, at least 180-fold, or at least 200-fold more resistant to degradation (e.g., nuclease degradation, e.g., in the presence of DNase I nuclease) than nanostructures that are non-covalently linked to oligolysine-PEG copolymers.

The relationship between amines of oligolysine and phosphates of nucleic acid nanostructures may be described in terms of an amine to phosphate ratio. The "N/P ratio," herein, refers is the ratio of positive (+) charges contributed to a structure by a primary, secondary or tertiary amine that can be protonated (e.g., in the side chain of a lysine) to negative (−) charges contributed to a nanostructure by phosphates of its nucleic acid backbone. For example, lysine in the middle of a peptide contributes 1+charge, while lysine at the N-terminus of a peptide contributes 2+charges. Thus, "subsaturated," refers to a N:P ratio of 0.95:1 or lower (i.e., lower number of amines compared to phosphates). "Saturated," by comparison, refers to a N:P ratio of 1:1 (i.e., the same number of amine compared to phosphates). "Supersaturated" refers to a N:P ratio of 1.05:1 or greater (i.e., greater number of amines compared to phosphates). Thus, in some embodiments, the ratio of amines or amines to phosphate (e.g., amines of oligolysine that interact with (e.g., are linked to) phosphates of a nucleic acid nanostructure backbone) is lower than 1:1. For example, the ratio of amines phosphates may be 0.9:1, 0.8:1, 0.7:1, 0.6:1, 0.5:1, 0.4:1, 0.3:1, 0.2:1 or 0.1:1. In some embodiments, the ratio of amines to phosphates is 0.9:1 to 0.1:1, 0.9:1 to 5:1, 0.8:1 to 0.1:1 or 0.5:1 to 0.1:1. In some embodiments, the ratio of amines or amines to phosphate (e.g., amines of oligolysine that interact with (e.g., are linked to) phosphates of a nucleic acid nanostructure backbone) is 1:1 or greater. In some embodiments, the ratio of amines or amines to phosphate (e.g., amines of oligolysine that interact with (e.g., are linked to) phosphates of a nucleic acid nanostructure backbone) is 1:1.

Thus, nucleic acid nanostructures provided herein, in some embodiments, are subsaturated with oligolysine-PEG copolymers at a N:P (nitrogen in lysine to phosphorus in nucleic acid) ratio of 0.1:1 to 0.95:1. As discussed above, nucleic acid nanostructures are considered to be "subsaturated" with oligolysine if less than 100% of the phosphates of the nucleic acid nanostructure backbone are linked to amines of oligolysine. In some embodiments, less than 98%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15% or less than 10% of the phosphates of nucleic acid nanostructure are linked to amines of the oligolysine. In some embodiments, 10% to 90%, 10% to 80%, 10% to 50%, 20% to 90%, or 20% to 80% of the phosphates of the nucleic acid nanostructure backbone are linked to amines of oligolysine.

In some embodiments, nucleic acid nanostructures provided herein are saturated with oligolysine-PEG copolymers (e.g., coated with oligolysine-PEG copolymers at a N:P (nitrogen in lysine to phosphorus in nucleic acid) ratio of 1:1). Thus, in some embodiments, nanostructures are covalently linked to (e.g., coated with) oligolysine-PEG copolymers at a N:P ratio of 0.1:1 to 1:1, 0.2 to 1:1, 0.3 to 1:1, 0.5 to 1:1, 0.75:1:1, 0.9:1 to 1:1, 0.95:1 to 1:10.1:1 to 0.95:1, 0.2:1 to 0.95:1, 0.5:1 to 0.95:1, 0.1:1 to 0.3:1, 0.2:1 to 0.4:1, 0.4:1 to 0.5:1, 0.5:1 to 0.75:1, 0.5:1 to 0.8:1, 0.6:1 to 0.8:1, 0.7:1 to 0.95:1, 0.8:1 to 0.95:1, or 0.9:1 to 0.95:1. In some embodiments, nanostructures are covalently linked to oligolysine-PEG copolymers at a N:P ratio of 1:1.

Nucleic acid nanostructures herein maintain their structural integrity (e.g., keep their original shape), despite their interactions with oligolysine-PEG copolymers. It should be understood that a nucleic acid nanostructure comprising oligolysine-PEG copolymers is herein considered to "maintain its structural integrity" if the shape of the nanostructure, under the same environmental conditions, can be distinguished/discerned for a period of time that is greater than that of a control nucleic acid nanostructure (e.g., a similar nucleic acid nanostructure that is not covalently linked to (e.g., coated with) oligolysine).

In some embodiments, the nucleic acid nanostructures are "supersaturated" with covalently linked oligolysine-PEG copolymers (e.g., coated with oligolysine-PEG copolymers at a N:P (nitrogen in lysine to phosphorus in nucleic acid) ratio of greater than 1:1) in a manner such that the architecture of the structures is not compromised. That is, nucleic acid nanostructures of the present disclosure have a 2D or 3D shape, despite the additional weight of and covalent interactions with positively-charged oligolysine-PEG copolymers.

Thus, nucleic acid nanostructures provided herein, in some embodiments, are supersaturated with oligolysine-PEG copolymers (e.g., coated with oligolysine-PEG copolymers at a N:P (nitrogen in lysine to phosphorus in nucleic acid) ratio of greater than 1:1). As discussed above, nucleic acid nanostructures are considered to be "supersaturated" with oligolysine-PEG copolymers if more than 100% of the phosphates of the nucleic acid nanostructure backbone are linked to amines of oligolysine-PEG copolymers. In some embodiments, 100% of the phosphates of nucleic acid nanostructure are linked to amines of the oligolysine-PEG copolymers. In some embodiments, 90% to 100%, 90% to 95%, or 95% to 100% of the phosphates of the nucleic acid nanostructure backbone are linked to amines of oligolysine-PEG copolymers. Further, as discussed above, nucleic acid nanostructures are considered to be "supersaturated" with oligolysine-PEG copolymers if, nanostructures are covalently linked to (e.g., coated with) oligolysine-PEG copolymers at a N:P ratio of 1.05:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1:9:1, 10:1, or greater. Thus, in some embodiments, nanostructures are covalently linked to (e.g., coated with) oligolysine-PEG copolymers at a N:P ratio of 1:1 to 2:1, 1:1 to 3:1, 1.1 to 5:1, 1.1:1 to 2:1, 1.1:1 to 3:1, 1.5:1 to 2:1, 1.5:1 to 3:1, 1.75:1 to 3:1, 1.75:1 to 5:1, 2:1 to 3:1, 3:1 to 4:1, 4:1 to 5:1, 6:1 to 7:1, or 5:1 to 10:1.

As used herein, the terms "nucleic acid" and/or "oligonucleotide" may refer to at least two nucleotides covalently linked together. A nucleic acid of the present disclosure may generally contain phosphodiester bonds, although in some cases, nucleic acid analogs are included that may have other backbones, comprising, for example, phosphoramide (Beaucage et al., *Tetrahedron* 49(10):1925 (1993) and references therein; Letsinger, J. *Org. Chem.* 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphophoroamidite linkages (see Eckstein, *Oligonucleotides and Analogues: A Practical Approach*, Oxford University Press), and peptide nucleic acid backbones and linkages (see Egholm, *J. Am. Chem. Soc.* 114:1895 (1992); Meier et al., *Chem. Int. Ed. Engl.* 31:1008 (1992); Nielsen, *Nature,* 365:566 (1993); Carlsson et al., *Nature* 380:207 (1996), all of which are incorporated by reference). Other analog nucleic acids include those with positive backbones (Denpcy et al., *Proc. Natl. Acad. Sci. USA* 92:6097 (1995); non-ionic backbones (U.S. Pat. Nos. 5,386,023, 5,637,684, 5,602,240, 5,216,141 and 4,469,863; Kiedrowski et al., Angew. *Chem. Intl.* Ed. English 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "Carbohydrate Modifications in Antisense Research", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., *Chem. Soc. Rev.* (1995) pp 169-176). Several nucleic acid analogs are described in Rawls, C & E News Jun. 2, 1997 page 35. All of these references are hereby expressly incorporated by reference. Nucleic acid may have a homogenous backbone (e.g., entirely phosphodiester or entirely phosphorothioate) or a heterogeneous (or chimeric) backbone. Phosphorothioate backbone modifications render a nucleic acid less susceptible to nucleases and thus more stable (as compared to a native phosphodiester backbone nucleic acid) under certain conditions. Other linkages that may provide more stability to a nucleic acid include without limitation phosphorodithioate linkages, methylphosphonate linkages, methylphosphorothioate linkages, boranophosphonate linkages, peptide linkages, alkyl linkages, dephospho type linkages, and the like. Thus, in some instances, nucleic acids have non-naturally occurring backbones. Modifications of the ribose-phosphate backbone may be done, for example, to facilitate the addition of labels, or to increase the stability and half-life of such molecules in physiological environments.

Nucleic acids may be single-stranded (ss) or double-stranded (ds), as specified, or may contain portions of both single-stranded and double-stranded sequence (e.g., are partially double-stranded). Nucleic acids may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, and isoguanine. As used herein, the term "nucleoside" includes nucleotides as well as nucleoside and nucleotide analogs, and modified nucleosides such as amino modified nucleosides. In addition, "nucleoside" includes non-naturally occurring analog structures. Thus, for example, the individual units of a peptide nucleic acid, each containing a base, are referred to herein as a nucleoside.

Nucleic acids include DNA such as B-form DNA, D-form DNA and L-form DNA and RNA, as well as various modifications thereof. Modifications include base modifications, sugar modifications, and backbone modifications. Non-limiting examples of these are provided below.

Non-limiting examples of DNA variants that may be used as provided herein are L-DNA (the backbone enantiomer of DNA, known in the literature), peptide nucleic acids (PNA) bisPNA clamp, a pseudocomplementary PNA, a locked nucleic acid (LNA), or co-nucleic acids of the above such as DNA-LNA co-nucleic acids. It is to be understood that nucleic acids used as provided herein may be homogeneous or heterogeneous in nature. As an example, they may be completely DNA in nature or they may comprise DNA and non-DNA (e.g., LNA) monomers or sequences. Thus, any combination of nucleic acid elements may be used. The nucleic acid modification may render the nucleic acid more stable and/or less susceptible to degradation under certain conditions. For example, in some instances, the nucleic acids are nuclease-resistant.

Methods of synthesizing nucleic acids (e.g., ssDNA or dsDNA, or ssRNA or dsRNA) are known in the art and are described, for example, in U.S. Pat. Nos. 5,143,854 and 5,445,934, herein incorporated in their entirety.

Nucleic acids may be synthesized in vitro. Methods for synthesizing nucleic acids, including automated nucleic acid synthesis, are also known in the art. Nucleic acids having modified backbones, such as backbones comprising phosphorothioate linkages, and including those comprising chimeric modified backbones may be synthesized using automated techniques employing either phosphoramidate or H-phosphonate chemistries. (F. E. Eckstein, "Oligonucleotides and Analogues—A Practical Approach" IRL Press, Oxford, UK, 1991, and M. D. Matteucci and M. H. Caruthers, *Tetrahedron Lett.* 21, 719 (1980)) Aryl- and alkyl-phosphonate linkages can be made, e.g., as described in U.S. Pat. No. 4,469,863; and alkylphosphotriester linkages (in which the charged oxygen moiety is alkylated), e.g., as described in U.S. Pat. No. 5,023,243 and European Patent No. 092,574, can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165; Crooke S T et al. (1996) Annu Rev Pharmacol Toxicol 36:107-129; and Hunziker J et al. (1995) Mod Synth Methods 7:331-417.

Nucleic acids may additionally or alternatively comprise modifications in their sugars. For example, a β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, arabinose, 2'-F-arabinose, 2'-O—($C_1$-$C_6$)alkyl-ribose, preferably 2'-O—($C_1$-$C_6$)alkyl-ribose is 2'-O-methylribose, 2'-O—($C_2$-$C_6$)alkenyl-ribose, 2'-[O—($C_1$-$C_6$)alkyl-O—($C_1$-$C_6$)alkyl]-ribose, 2'-$NH_2$-2'-deoxyribose, β-D-xylo-furanose, α-arabinofuranose, 2,4-dideoxy-β-D-erythro-hexo-pyranose, and carbocyclic (described, for example, in Froehler J (1992) Am Chem Soc 114:8320) and/or open-chain sugar analogs (described, for example, in Vandendriessche et al. (1993) Tetrahedron 49:7223) and/or bicyclosugar analogs (described, for example, in Tarkov M et al. (1993) Helv Chim Acta 76:481).

Nucleic acids may comprise modifications in their bases. Modified bases include modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1,2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'-β-D-2'-deoxyribofuranosyl)-2(1H)-pyridone, and its Watson-Crick complement dP, the purine analog, is 2-amino-8-(1'-β-D-1'-deoxyribofuranosyl)-imidazo[1,2-a]-1,3,5-triazin-4(8H)-one.

In exemplary embodiments, nucleic acid nanostructures comprise single-stranded genomic DNA. For example, nucleic acid nanostructures may comprise linear or circular single-stranded M13 plasmid DNA. In some embodiments, nucleic acid nanostructures do not comprise plasmid DNA.

It should be appreciated that nucleic acid nanostructures of the present disclosure, in some embodiments, do not include condensed nucleic acid. As used herein, "condensed nucleic acid" refers to compacted nucleic acid, for example, that is twisted and coiled upon itself (see, e.g., Teif V B, et al. *Progress in Biophysics and Molecular Biology* 105 (3): 208-222, incorporated by reference herein). The term "condensed nucleic acid" excludes nucleic acid nanostructures that have a distinct 2D or 3D architecture.

It should also be appreciated that nucleic acid nanostructures of the present disclosure, in some embodiments, do not include coding nucleic acid. That is, in some embodiments, nucleic acid nanostructures comprise non-coding nucleic acids (e.g., nucleic acids that do not encode proteins). As used herein, a "coding nucleic acid" refers to a nucleic acid containing a nucleotide sequence that specifies a sequence of amino acids of a protein (e.g., a therapeutic protein). Thus, a "non-coding nucleic acid" is a nucleic acid that does not specify a sequence of amino acids of a protein and, accordingly, is not transcribed into RNA or translated into protein.

In other embodiments, it should be understood that a nucleic acid nanostructure may contain one or more coding nucleic acids.

In some embodiments, nucleic acids used to make nucleic acid nanostructures do not code for any amino acid. In some embodiments, nucleic acids used to make nucleic acid nanostructures do not code for more than 1, 2, 3, 4 or 5 consecutive amino acids.

In some embodiments, nucleic acids used to make nucleic acid nanostructures do not include art-recognized regulatory elements/sequences such as promoters, enhancers, polyA sequences and/or ribosomal binding site sequences.

In some embodiments, nucleic acids used to make nucleic acid nanostructures are not plasmids.

In some embodiments, nucleic acids used to make nucleic acid nanostructures contain more than one nucleic acid, and the nucleic acid are different from each other. That is, the nucleic acids of a nucleic acid nanostructure may comprise a plurality of different nucleic acids.

In some embodiments, nucleic acid nanostructures are not encapsulated by or linked to (e.g., coated with) lipids. For example, a variety of gene delivery methods of the prior art make use of nucleic acid nanostructures that are linked to hydrophobic moieties and/or covered by lipids (e.g., such as a lipid bilayer), which function to prevent nuclease degradation (see, e.g., WO 2013148186 A1). The present disclosure, in some embodiments, excludes nucleic acid nanostructures that are linked to hydrophobic moieties and/or covered by lipids. In other embodiments, however, a nucleic acid nanostructure may contain one or more nucleic acids linked to one or more hydrophobic moieties and/or lipids.

Nucleic acid nanostructures of the present disclosure have a variety of in vitro and in vivo uses. In some embodiments, may be used as scaffolds, cages or multifunctional carriers for delivering an agent (e.g., therapeutic agent) that is intended for use in vivo and/or in vitro. A nucleic acid nanostructure may be delivered by any suitable delivery method, for example, intravenously or orally. As used herein, an agent is any atom, molecule, or compound that can be used to provide benefit to a subject (including without limitation prophylactic or therapeutic benefit) or that can be used for diagnosis and/or detection (for example, imaging) in vivo, or that may be used for effect in an in vitro setting (for example, a tissue or organ culture, a clean-up process, and the like). Agents may be, without limitation, therapeutic agents and/or diagnostic agents. In some embodiments, an agent is a therapeutic agent, a prophylactic agent and/or a diagnostic agent. In some embodiments, an agent is a targeting molecule. Examples of agents for use with any one of the embodiments described herein are described below.

The present disclosure contemplates imparting addressability to nucleic acid nanostructures. For example, nucleic acid nanostructures may be modified by site-specific attachment of targeting moieties such as proteins, ligands or other small biomolecules. In some embodiments, nucleic acid nanostructures may comprise nucleic acid "staple" strands, as described above, that serve as handles for nanometer-specific placement of accessory molecules (e.g., biotin/streptavidin) at virtually any position on or within the structure (see, e.g., Stein et al. *Chemphyschem*. 12(3), 689-695 (2011); Steinhauer et al. *Angew Chem. Int. Ed. Engl.* 48(47), 8870-8873 (2009); Stein et al. *J. Am. Chem. Soc.* 133(12), 4193-4195 (2011); Kuzyk et al. *Nature* 483(7389), 311-314 (2012); and Ding et al. *J. Am. Chem. Soc.* 132(10), 3248-3249 (2010); Yan et al. *Science* 301(5641), 1882-1884 (2003); and Kuzuya et al. *Chembiochem*. 10(11), 1811-1815 (2009), each of which is incorporated by reference herein).

In some embodiments, nucleic acids of nanostructures provided herein may be modified (e.g., covalently modified) with a linker (e.g., biotin linker) during synthesis or via enzymatic means (see, e.g., Jahn et al. *Bioconjug. Chem.* 22(4), 819-823 (2011) incorporated by reference herein). Such methods may also be used to position reaction systems on nucleic acid nanostructures through the chemical biotinylation of enzyme molecules (see, e.g., Voigt et al. *Nat. Nanotechnol.* 5(3), 200-203 (2010)).

A more generalized antibody-based binding approach may also be used to link target proteins to nucleic acid nanostructures at defined distances (see, e.g., Williams et al. *Angew Chem. Int. Ed. Engl.* 46(17), 3051-3054 (2007); and He Y et al. *J. Am. Chem. Soc.* 128(39), 12664-12665 (2006), each of which is incorporated by reference herein). Thus, in some embodiments, nucleic acid nanostructures may be linked to one or more antibodies.

In other embodiments, DNA aptamers, which adopt a specific secondary structure with high binding affinity for a particular molecular target, may be used as linkers, thereby eliminating the need for protein linkers (see, e.g., Ellington et al. *Nature* 346(6287), 818-822 (1990); Chhabra et al. *J. Am. Chem. Soc.* 129(34), 10304-10305 (2007); and Rinker et al. *Nat. Nanotechnol.* 3(7), 418-422 (2008), each of which is incorporated by reference herein).

The present disclosure also contemplates the use of recombinant genetic engineering methods to selectively add affinity tags or other peptide linkers to nucleic acid nanostructures. For example, polyhistidine sequence consisting of multiple histidine residues on the C- or N-terminus end of a target protein is a commonly used tag for affinity-based purification. This, in turn, can be linked via nickel-mediated interaction to a nitrilotriacetic acid molecule that is covalently conjugated to an amine (see, e.g., Goodman et al. *Chembiochem*. 10(9), 1551-1557 (2009), incorporated by reference herein) or thiol-modified (see, e.g., Shen et al. *J. Am. Chem. Soc.* 131(19), 6660-6661 (2009), incorporated by reference herein) nucleic acid. Through this method, fluorescent proteins may be positioned both periodically and specifically on nucleic acid nanostructures (Goodman et al. (2009); and Shen et al. (2009)). Similarly, SNAP and HaloTag® peptide sequences, also used for affinity purification of recombinant proteins, may be utilized for the orthogonal decoration of nucleic acid nanostructures with different protein or enzyme species (see, e.g., Sacca et al. *Angew Chem. Int. Ed. Engl.* 49(49), 9378-9383 (2010), incorporated by reference herein). A related approach involving the creation of chimeric proteins conjugated to a DNA-binding domain, can eliminate the often complex chemical synthesis techniques and toxic compounds (e.g., nickel) necessary to stably conjugate affinity tag binding partners to oligonucleotide strands. Further, zinc-finger domains that recognize specific double-stranded sequences may be used to arrange fluorescent proteins at specific locations on nucleic acid nanostructures of the present disclosure (see, e.g., Nakata et al. *Angew Chem. Int. Ed. Engl.* 51(10), 2421-2424 (2012), incorporated by reference herein).

An agent may be covalently or non-covalently attached to a nucleic acid nanostructure. The location and nature of the linkage between the agent and the nucleic acid nanostructure will depend upon the function of the agent. As an example, an agent may be intended to release (including slow release) from the nanostructure, and in that case, the linkage between the agent and the nanostructure may be chosen to achieve the desired release profile. In some embodiments, an agent may be inactive in its bound form and activated only when released.

In some embodiments, an agent may be combined with nucleic acids during assembly (e.g., self-assembly) of nanostructures, or an agent may be combined with pre-formed nucleic acid nanostructures.

Agents may be linked to an interior surface (in the interior compartment) or an exterior surface of a nanostructure. Agents may be arranged in various configurations. Upon hybridization of handles to anti-handles, agents become indirectly linked to nucleic acid nanostructures. In some embodiments, the exterior surface of a nanostructure contains a combination of adjuvant molecules (e.g., CpG oligonucleotides) and targeting molecules (e.g., antibody fragments such as scFv fragments), and the interior surface of the nanostructure contains a combination of tracking dye and antigen. It should be understood that nanostructures of the present disclosure permit precise placement of an agent or more than one agent (e.g., a combination of different agents) on the interior and/or exterior surface of the nanostructures.

Nucleic acid nanostructures of the present disclosure permit high-density "packing" of agent on and into the nanostructures. In some embodiments, a nucleic acid nanostructures is decorated with one agent per 50 $nm^2$ to 75 $nm^2$. In some embodiments, a nucleic acid nanostructure is decorated with one agent per 50 $nm^2$, 55 $nm^2$, 60 $nm^2$, 65 $nm^2$, 70 $nm^2$ or 75 $nm^2$. For example, using a rhombic-lattice spacing for a 30 nm tall, 60 nm diameter cylindrical nanostructure, 72 positions on the exterior of the nanostructure and 84 positions on the interior may be occupied by agent.

The present disclosure contemplates, in some aspects, the delivery of nucleic acid nanostructures, or nucleic acid nanostructures loaded with an agent, systemically or to localized regions, tissues or cells. Any agent may be delivered using the methods of the present disclosure provided that it can be loaded onto or into the nucleic acid nanostructure. Because such processes are relatively innocuous, it is expected that virtually any agent may be used.

An agent for use in accordance with the present disclosure may be a protein-based agent (including a protein), a nucleic-acid based agent (including a nucleic acid), a chemical-based agent (including chemical compounds) or combination of any two or more of the foregoing. For example, an agent may be an antibody-drug conjugate. An "antibody-drug conjugate" is a complex of an antibody (e.g., a whole monoclonal antibody (mAb) or an antibody fragment such as a single-chain variable fragment (scFv)) linked to a biologically-active small molecule (e.g., small molecule drug).

Examples of protein-based and peptide-based agents (e.g., therapeutic, prophylactic and/or diagnostic protein-based agents) for use in accordance with the present disclosure include, without limitation, antibodies (e.g., monoclonal antibodies, chimeric antibodies, humanized antibodies), antibody fragments (e.g., single- or multi-chain antibodies, antibody fragments such as Fab fragments, Fc fragments), enzymes, co-factors, receptors, ligands, transcription factors and other regulatory factors, antigens, cytokines, chemokines and hormones.

Examples of nucleic acid-based agents (e.g., therapeutic, prophylactic and/or diagnostic nucleic acid-based agents) for use in accordance with the present disclosure include, without limitation, RNA interference molecules such as short-interfering RNA (siRNA) molecules, short-hairpin RNA (shRNA) molecules, and micro RNA (miRNA) molecules. Nucleic acid-based agents may be recombinant (e.g., non-naturally occurring molecule produced by joining two different nucleic acids) or synthetic (e.g., chemically or otherwise synthesized).

Examples of chemical-based agents (e.g., therapeutic, prophylactic and/or diagnostic chemical-based agents) for use in accordance with the present disclosure include, without limitation, small molecules (e.g., small molecule drugs). A "small molecule" is a low molecular weight (e.g., <900 Daltons) organic compound.

A "therapeutic agent" is an agent used to treat a condition in a subject (e.g., human or non-human subject). A "prophylactic agent" is an agent used to prevent a condition in a subject (e.g., human or non-human subject). Examples of therapeutic agents and prophylactic agents for use in accordance with the present disclosure include, without limitation, antibodies, antibody fragments, other proteins and peptides, lipids, carbohydrates, small molecules, polymers, metal nanoparticles, RNA interference molecules (e.g., siRNAs, shRNAs, miRNAs), antisense molecules, antigens (e.g., peptide antigens), adjuvants (e.g., CpG oligonucleotides), anti-neoplastic agents, anti-cancer, anti-infective agents (e.g., anti-microbial agents, anti-bacterial agents), anti-fungal agents, anti-viral agents (e.g., anti-retroviral agents), anti-inflammatory agents, metabolic agents, immunomodulatory agents (e.g., immunostimulatory agents, immunosuppressive agents), anti-hypertensive agents, anti-Alzheimer's agents, and anti-Parkinson's agents.

An "adjuvant" is an agent that enhances an immune response to an antigen. In some embodiments, an adjuvant is a CpG oligonucleotide. CpG oligonucleotides are short single-stranded synthetic DNA molecules that contain a cytosine triphosphate deoxynucleotide ("C") followed by a guanine triphosphate deoxynucleotide ("G"). The "p" refers to the phosphodiester, or modified phosphorothioate (PS), linkage between consecutive nucleotides. CpG oligonucleotides typically enhance the immunostimulatory effect of nucleic acid nanostructures (Li, J. et al. ACS NANO, 5(11): 8783-8789, 2011; Schuller, V. et al. ACS NANO, 5(12): 9696-9702, 2011). For example, after they are taken up by cells, CpG oligonucleotides, which are a hallmark of microbial DNA, are recognized by the endosomal Toll-like receptor 9 (TLR9) that activates downstream pathways to induce immunostimulatory effects, producing high-level secretion of various pro-inflammatory cytokines including tumor necrosis factor (TNF)-$\alpha$, interleukin (IL)-6, and IL-12. In some embodiments, CpG oligonucleotides are linked to an interior surface of a nucleic acid nanostructure. In some embodiments, CpG oligonucleotides are linked to an exterior surface of a nucleic acid nanostructure. In some embodiments, a nucleic acid nanostructure has CpG oligonucleotides linked to both an interior and exterior surface. Other examples of adjuvants include, without limitation, lipopolysaccharide and polyI:C (dsRNA mimic).

A "diagnostic agent" is an agent used to diagnose a condition in a subject (e.g., human or non-human subject). Examples of therapeutic agents and prophylactic agents for use in accordance with the present disclosure include, without limitation, imaging agents (e.g., contrast agents, radioactive agents, tracking dyes (e.g., fluorescent dyes)). An "imaging agent" is an agent that emits signal directly or indirectly thereby allowing its detection in vivo. Imaging agents, such as contrast agents and radioactive agents, can be detected using medical imaging techniques such as nuclear medicine scans and magnetic resonance imaging (MRI). Imaging agents for magnetic resonance imaging (MRI) include Gd(DOTA), iron oxide or gold nanoparticles;

imaging agents for nuclear medicine include 201 Tl, gamma-emitting radionuclide 99 mTc; imaging agents for positron-emission tomography (PET) include positron-emitting isotopes, (18)F-fluorodeoxyglucose ((18)FDG), (18)F-fluoride, copper-64, gadoamide, and radioisotopes of Pb(II) such as 203Pb, and 1 1In; imaging agents for in vivo fluorescence imaging such as fluorescent dyes or dye-conjugated nanoparticles. In some embodiments, an agent to be delivered is conjugated, or fused to, or mixed or combined with an imaging agent.

An agent may be naturally occurring or non-naturally occurring (e.g., chemical compounds that are non-naturally occurring). Naturally occurring agents include those capable of being synthesized by the subjects to whom nucleic acid nanostructures are administered. Non-naturally occurring are those that do not exist in nature normally, whether produced by plant, animal, microbe or other living organism. It should be understood that nucleic acid nanostructures that comprise naturally-occurring agents are considered, as a whole, to be non-naturally occurring.

An agent may be, without limitation, a chemical compound including a small molecule, a protein, a polypeptide, a peptide, a nucleic acid (e.g., siRNA, shRNA, microRNA), a virus-like particle, a steroid, a proteoglycan, a lipid, a carbohydrate, and analogs, derivatives, mixtures, fusions, combinations or conjugates thereof. An agent may be a prodrug that is metabolized and thus converted in vivo to its active (and/or stable) form. The present disclosure further contemplates the loading of more than one type of agent in a nucleic acid nanostructure and/or the combined use of nanostructures comprising different agents.

A variety of agents that are currently used for therapeutic or diagnostic purposes can be delivered according to the present disclosure and these include, without limitation, imaging agents, immunomodulatory agents such as immunostimulatory agents and immunoinhibitory agents (e.g., cyclosporine), antigens, adjuvants, cytokines, chemokines, anti-cancer agents, anti-infective agents, nucleic acids, antibodies or fragments thereof, fusion proteins such as cytokine-antibody fusion proteins, Fc-fusion proteins, analgesics, opioids, enzyme inhibitors, neurotoxins, hypnotics, anti-histamines, lubricants, tranquilizers, anti-convulsants, muscle relaxants, anti-Parkinson agents, anti-spasmodics, muscle contractants including channel blockers, miotics and anti-cholinergics, anti-glaucoma compounds, modulators of cell-extracellular matrix interactions including cell growth inhibitors and anti-adhesion molecules, vasodilating agents, inhibitors of DNA, RNA or protein synthesis, anti-hypertensives, antipyretics, steroidal and non-steroidal anti-inflammatory agents, anti-angiogenic factors, antisecretory factors, anticoagulants and/or antithrombotic agents, local anesthetics, ophthalmics, prostaglandins, targeting agents, neurotransmitters, proteins, cell response modifiers and vaccines. It should be understood that any one or more of the foregoing agents may be specifically excluded from nucleic acid nanostructures of the present disclosure.

A "targeting molecule" is a molecule that directs a nucleic acid nanostructure to a target cell of interest. Targeting molecules that target cell types, such as, for example, dendritic cells, tumor cells, T cells, B cells and natural killer (NK) cells are contemplated herein. In some embodiments, a targeting molecule binds specifically to extracellular cognate molecules present on target cells. Examples of targeting molecule for use in accordance with the present disclosure include, without limitation, antibodies, antibody fragments and ligands. It should be understood that a nucleic acid nanostructure of the present disclosure may have one or more than one (e.g., a combination of different) targeting molecules.

In some embodiments, a nucleic acid nanostructure comprises a targeting molecule, an antigen and an adjuvant. For example, a nucleic acid nanostructure may comprise a single chain antibody fragments (scFv) that binds specifically to DEC205, an antigen (e.g., peptide antigen), and CpG oligonucleotides.

When nucleic acid nanostructures of the present disclosure are used in vivo, they can be administered to virtually any subject type that is likely to benefit prophylactically, therapeutically or prognostically from the delivery of nucleic acid nanostructures as contemplated herein.

A "subject" to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other non-human animals, for example mammals (e.g., primates (e.g., cynomolgus monkeys, rhesus monkeys), including commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In some embodiments, the non-human animal is a mammal. The non-human animal may be a male or female and at any stage of development. A non-human animal may be a transgenic animal.

In some embodiments, subjects to whom nucleic acid nanostructures are administered may have or may be at risk of developing condition that can be diagnosed or that can benefit or that can be prevented from systemic or localized delivery of one or more particular agents. Such conditions include cancer (e.g., solid tumor cancers), infections (e.g., particularly infections localized to particular regions or tissues in the body), autoimmune disorders, allergies or allergic conditions, asthma, transplant rejection, diabetes and/or heart disease.

In some embodiments, agents are delivered to prevent the onset of a condition whether or not such condition is considered a disorder.

In some embodiments, subjects may be in need of an implant or may have already received an implant, and nucleic acid nanostructures of the present disclosure are to be used in conjunction with such implant therapy.

Nucleic acid nanostructures and compositions containing nucleic acid nanostructures may be administered to a subject (e.g., a human or non-human subject) subcutaneously or intravenously (e.g., single/multiple injection(s) or continuous infusion), or by other means.

In some embodiments, nucleic acid nanostructures are administered to a subject as a component of a polymeric gel composition. The polymeric gel composition may be biocompatible and/or biodegradable. In some embodiments, the polymeric gel composition is formed from, and/or comprises at least one polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-epsilon-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly (vinylpyrrolidone) and copolymers of the above, including graft copolymers (see, e.g., International Publication No. WO2009102465).

In some embodiments, the present disclosure provides methods for manipulating, directly in the body, dendritic-cell recruitment and activation. Immature dendritic cells patrol peripheral tissues, and on uptake of foreign substances (e.g., antigen), they may mature to express on their surface molecules (e.g., the receptor CCR7 and major histocompatibility complex (MHC) antigen) to facilitate lymph-node homing and subsequent antigen presentation to T-cells, respectively. Elements of infection that mobilize and activate dendritic cells include inflammatory cytokines, and "danger signals" related specifically to the infectious agent. Cytosine-guanosine oligonucleotide (CpG-ODN) sequences are uniquely expressed in bacterial DNA, and are potent danger signals that stimulate mammalian dendritic-cell activation and dendritic-cell trafficking. Thus, in some embodiments, the present disclosure provides methods for administering to a subject nucleic acid nanostructures that comprise antigen (e.g., cancer antigen) and danger signals (e.g., CpG oligonucleotides).

Some aspects of the present disclosure provide compositions that comprise any one or more nucleic acid nanostructures covalently linked to (e.g., coated with) oligolysine-PEG copolymers. Compositions provided herein, in some embodiments, comprise a solution that contains physiological levels of salt. For example, a solution may comprise 0.1 mM to 0.9 mM magnesium ($Mg^{2+}$) (e.g., 0.1 mM, 0.2 mM, 0.3 mM, 0.4 mM, 0.5 mM, 0.6 mM, 0.7 mM, 0.8 mM or 0.9 mM $Mg^{2+}$). In some embodiments, a solution comprises (or further comprise) 0.5 mM to 1.5 mM calcium ($Ca^{2+}$). For example, a solution may comprise 0.5 mM, 0.6 mM, 0.7 mM, 0.8 mM, 0.9 mM, 1.0 mM, 1.1 mM, 1.2 mM, 1.3 mM, 1.4 mM or 1.5 mM $Ca^{2+}$.

The present disclosure provides pharmaceutical compositions. Pharmaceutical compositions are sterile compositions that comprise nucleic acid nanostructures that are covalently linked to (e.g., coated with) oligolysine-PEG copolymers and, in some embodiments, agent(s). In some embodiments, pharmaceutical compositions comprise a pharmaceutically-acceptable carrier. A pharmaceutically-acceptable carrier facilitates administration of the nucleic acid nanostructures.

Nucleic acid nanostructures, when delivered systemically, may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients.

Nucleic acid nanostructures of the present disclosure (including compositions comprising the nanostructures) may be used in a variety of applications, including biomedical applications such as nanomedicine. For example, nucleic acid nanostructures may be used for drug delivery (e.g., targeted drug delivery), immunotherapy, diagnostics and molecular biology (for a review, see, e.g., Smith D. et al. *Nanomedicine* (Lond). 2013 January; 8(1):105-21, incorporated by reference herein). In some embodiments, nucleic acid nanostructures may be used as scaffold-based biosensors (see, e.g., Pei H. et al. *NPG Asia Materials* (2013) 5, 1-8, incorporated by reference herein)

Nucleic acid nanostructures of the present disclosure may be used to investigate cellular mechanism, or they may be use in the field of material sciences. For example, the present disclosure contemplates the assembly of chiral plasmonic nanostructures with tailored optical response (see, e.g., Liedl et al. 2012 *Nature,* 483, 311, incorporated by reference herein), assembly of anistropic plasmonic nanostructures (see, e.g., Pal et al. 2011 *J. Am. Chem. Soc.* 133, 17606-17609, incorporated by reference herein), and layer-by-layer growth of superparamagnetic and fluorescently barcoded nanostructures (see, e.g., Wang et al. 2007 *Nanotechnology* 18, 40, 405026, incorporated by reference herein).

ADDITIONAL EMBODIMENTS

1. A DNA nanostructure coated and covalently cross-linked with oligolysine-polyethylene glycol (PEG) copolymer at a N:P (nitrogen in lysine to phosphorus in nucleic acid) ratio of 0.1:1 to 1:1.

2. The DNA nanostructure of paragraph 1, wherein primary amines of the DNA nanostructure form amine bonds with the oligolysine-PEG copolymer.

3. The DNA nanostructure of paragraph 1 or 2, wherein the DNA nanostructure has a half-life that is at least 10000-fold greater than the half-life of an uncoated DNA nanostructure.

4. The DNA nanostructure of any one of paragraphs 1-3, wherein the DNA nanostructure has a half-life that is at least 180-fold greater than the half-life of a DNA nanostructure coated but not crosslinked with oligolysine-PEG copolymer.

5. The DNA nanostructure of any one of paragraphs 1-4, wherein the DNA nanostructure maintains structural stability for at least 24 hours, at least 48 hours, or at least 72 hours in a physiological buffer comprising less than 0.5 mM $Mg^{2+}$.

6. The DNA nanostructure of any one of paragraphs 1-5, wherein the DNA nanostructure is a three-dimensional DNA nanostructure.

7. The DNA nanostructure of any one of paragraphs 1-6, wherein the DNA nanostructure has a void volume of at least 25%.

8. The DNA nanostructure of any one of paragraphs 1-7, wherein the oligolysine comprises 5 to 20 lysines.

9. The DNA nanostructure of paragraph 8, wherein the oligolysine comprises at least 10 lysines.

10. The DNA nanostructure of any one of paragraphs 1-8, wherein the PEG is PEG1K, PEG5K, PEG10K, or PEG20K.

11. The DNA nanostructure of paragraph 10, wherein the PEG is PEG5K.

12. A composition comprising a physiological buffer comprising less than 0.5 mM $Mg^{2+}$ and a DNA nanostructure coated and covalently crosslinked with oligolysine-PEG copolymer at a N:P (nitrogen in lysine to phosphorus in nucleic acid) ratio of 0.1:1 to 1:1.

13. The composition of paragraph 12 further comprising DNase I, optionally at a concentration of 300-1000 U/L.

14. A method comprising administering to a subject the DNA nanostructure of any one of paragraphs 1-11.

15. The method of paragraph 14, wherein the subject is a human subject.

16. The method of paragraph 14 or 15, wherein the DNA nanostructure is administered subcutaneously or intravenously.

17. A method comprising delivering to cells the DNA nanostructure of any one of paragraphs 1-11.

18. A method comprising coating a DNA nanostructure with oligolysine-PEG copolymer, and crosslinking the oligolysine-PEG copolymer to the DNA nanostructure using glutaraldehyde to form imine bonds with primary amines in the oligolysine-PEG copolymer.

19. The method of paragraph 18 further comprising reducing the imine bonds to amine bonds using a reducing agent, optionally wherein the reducing agent is sodium borohydride or sodium cyanoborohydride.

20. A method of producing a DNA nanostructure coated and covalently crosslinked oligolysine-PEG, the method comprising:
(i) adding oligolysine-PEG to a solution comprising a DNA nanostructure;
(ii) adding a crosslinking agent to the solution of (i); and
(iii) adding a reducing agent to the solution of (ii) to produce a three-dimensional nucleic acid nanostructure coated and covalently crosslinked oligolysine-PEG.

EXAMPLES

Example 1. Covalent Crosslinking of Polylysine Polymer Reduces Dissociation of Polymer from Nucleic Acid Nanostructures and Improves Stability Oligolysine comprising PEG5K interact with nanostructures through electrostatic attraction. In low $[Mg^{2+}]$ conditions, amines in the polylysine polymer can substitute for divalent cations and stabilize the electrostatic repulsions. However, since the binding between the polymer and the nanostructure is electrostatic, it is reversible. In order to decrease the dissociation of polymer from nanostructure (off-rate), the ability of different crosslinking agents (cisplatin, methoxypsoralen (8-MOP), formaldehyde, and glutaraldehyde) to covalently link a C-shaped $K_{10}$-PEG5K coated nanostructure (cDN) was determined under denaturing conditions. As shown in the PAGE assay of FIG. 1D, each crosslinking agent provided a concentration-dependent increase in stability, with the best results provided when using formaldehyde and glutaraldehyde.

In these crosslinking reactions, an aldehyde crosslinking agent, e.g. glutaraldehyde, forms imines bonds with primary amines in the oligolysine (FIG. 1E). These imine bonds decrease the off-rate of the $K_{10}$-PEG5K polymer, but can act as a Schiff base and are thus are reversible. In order to form covalent bonds, these imines may be reduced using a reducing agent, e.g., sodium borohydride or sodium cyanoborohydride, to form amine bonds (effectively irreversible under physiological conditions). Both the crosslinking and reduction steps are generalizable, scalable, and can be performed without specialized equipment at room temperature (FIG. 1F).

As shown in FIG. 1G, nucleic acid nanostructures that are covalently linked to (e.g., coated with) oligolysine-PEG copolymers demonstrate superior stability relative to bare nanostructures or nucleic acid nanostructures that are linked non-covalently to oligolysine-PEG copolymers. Provided are negative stain transmission electron microscopy (TEM) images of barrel shaped nucleic acid nanostructures—without polymer coating (bare DN), with non-covalent polymer ($K_{10}$-PEG5K) coating (cDN), with covalent polymer ($K_{10}$-PEG5K) coating (ccDN), and with covalent polymer ($K_{10}$-PEG5K) coating following reduction by sodium borohydride (rccDN).

Figures 2A, 2B, 2C, 2D:
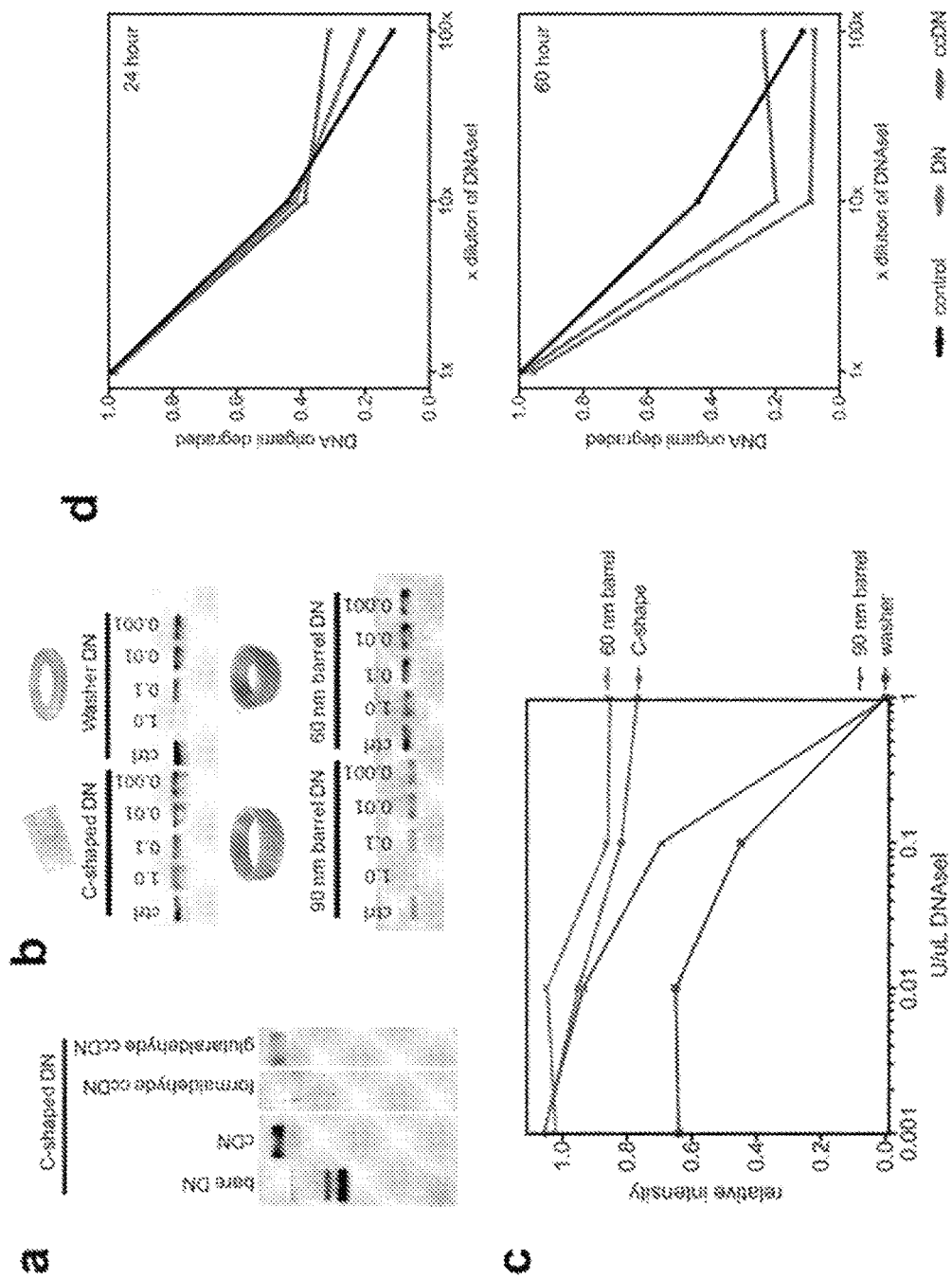
FIG. 2A shows a PAGE assay of bare (DN), non-covalent polymer ($K_{10}$-PEG5K) coated (cDN), and covalent polymer ($K_{10}$-PEG5K) coated (mediated by formaldehyde or glutaraldehyde) (ccDN) C-shaped nanostructures following a 90-min incubation with DNase I nuclease.
FIG. 2B shows PAGE assays of a variety of covalent polymer ($K_{10}$-PEG5K) coated nucleic acid nanostructures following 90-min incubations with varying concentrations of DNase I nuclease (in U/μL).
FIG. 2C shows quantification of the PAGE assays of FIG. 2B.
FIG. 2D shows quantification of a PAGE assay of bare (DN) and covalent polymer ($K_{10}$-PEG5K) coated (ccDN) nucleic acid nanostructures following 24- and 60-hour incubations with varying dilutions of DNase I.

Example 2. Covalent Crosslinking of Polylysine Polymer Improves Stability of Nucleic Acid Nanostructures Under Strenuous Nuclease Conditions Bare (DN), non-covalent polymer ($K_{10}$-PEG5K) coated (cDN), and covalent polymer ($K_{10}$-PEG5K) coated (mediated by formaldehyde or glutaraldehyde) (ccDN) C-shaped nanostructures were incubated for 90-min at 37° C. with DNase I nuclease. As shown in FIG. 2A, covalently coated C-shaped nanostructures that were crosslinked using glutaraldehyde provided increased protection of the nanostructure compared to nanostructures crosslinked with formaldehyde.

Four different nucleic acid nanostructures (C-shaped, Washer, 90 nm barrel, and 60 nm barrel) were covalently linked to (e.g., coated with) a saturating amount of $K_{10}$-PEG5K polymer (e.g., N:P ratio of 1:1) using formaldehyde or glutaraldehyde. Following covalent crosslinking reactions, performed as described in Example 1 using glutaraldehyde, covalently coated nanostructures (ccDN) were buffer exchanged into phosphate buffered saline prior to performing subsequent experiments with nucleases. Each of the four nanostructures were incubated with varying concentrations of DNase I (0.001, 0.01, 0.1, and 1.0 U/µL) for 90 min at 37° C. Interestingly, the degradation rates varied dramatically (FIGS. 2B-2C), with the 60 nm barrel and C-shaped nanostructures maintaining the highest levels of structural integrity at highest levels of DNase I.

Bare (DN) and covalent polymer ($K_{10}$-PEG5K) coated (ccDN) nucleic acid nanostructures were incubated for 24- and 60-hours with varying dilutions of DNase I (1× dilution, 10× dilution, and 100× dilution) (FIG. 2D). Notably, covalent polymer ($K_{10}$-PEG5K) coated (ccDN) nucleic acid nanostructures were significantly more resistant to DNase I degradation at high concentrations (100× dilution) than bare nanostructures.

Example 3. Covalent Crosslinking of Polylysine-PEG Copolymer Improves Stability of Nucleic Acid Nanostructures Under Strenuous Nuclease Conditions A 60 nm barrel-like nanostructure was used to assess structural integrity by FRET. In this structure, 3'-ends of alternate DNA oligonucleotides in the inner helices of the barrel were functionalized with Cy5 fluorophores. The remaining inner helix oligonucleotides were functionalized with Cy3 at the 5'-end. The distance between adjacent Cy3 (donor) and Cy5 (acceptor) fluorophores is less than the Förster distance of 5.6 nm, whereas the distance between non-adjacent fluorophores is approximately 8 nm. Thus, a fully intact barrel would bring the Cy3 and Cy5 fluorophores sufficiently proximal to one another such that FRET occurs upon excitation of the Cy3 fluorophore to provide substantial Cy5 emission. Meanwhile, a degraded barrel nanostructure would cause the distance between the FRET pair to exceed the 5.6 nm Förster distance, bringing a loss of Cy5 emission. Therefore, one can use an observation of Cy3 excitation and subsequent Cy5 emission as a proxy for the structural integrity of the barrel nanostructure. Non-covalent polymer coated 60 nm barrel nucleic acid nanostructures ($K_{10}$PEG5K+DNaseI) and covalent polymer coated 60 nm barrel nucleic acid nanostructures ($K_{10}$PEG5K+crosslink+DNaseI) were incubated in the presence of 0.2 U/µL DNase I for 72 hours. During the incubation periods, the Cy5 emission spectra were monitored. Notably, no measurable degradation was observed for the nanostructure covalently linked to (e.g., coated with) polymer. Meanwhile, a half-life of ~6 hours was observed for degradation of the nanostructure non-covalently linked to (e.g., coated with) polymer.

Figures 3A, 3B:
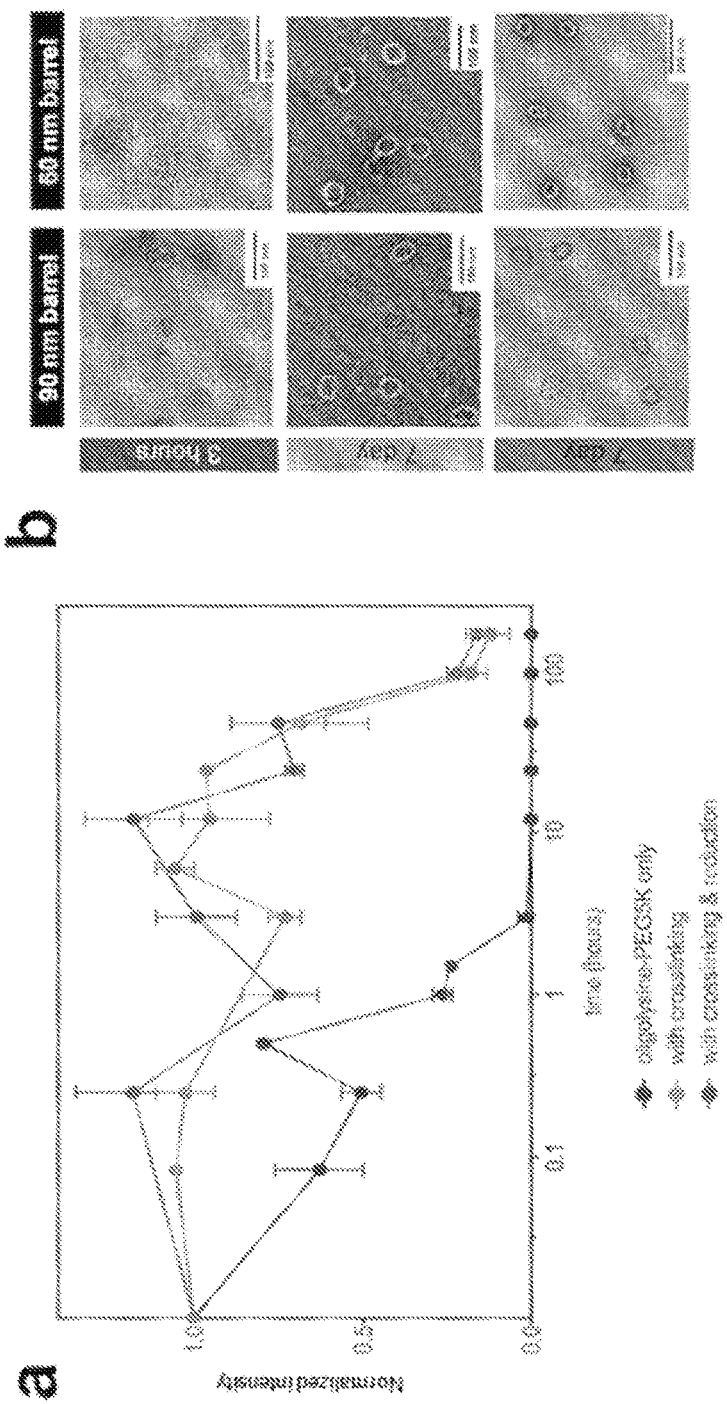
FIG. 3A shows a graph of normalized intensities of quantified PAGE assays demonstrating the survival of 90 nm barrel nucleic acid nanostructures when incubated with 1 U/μL DNase I at 37° C. over time. Nanostructures coated with covalent polymer ($K_{10}$-PEG5K) are significantly more resistant to degradation than nanostructures coated with non-covalent polymer ($K_{10}$-PEG5K).
FIG. 3B shows negative stain TEM images of nanostructures after incubation at 37° C. with 1 U/μL DNase I. At the top are nanostructures coated with non-covalent polymer ($K_{10}$-PEG5K) after 3 hours of incubation; in the middle are nanostructures coated with covalent polymer ($K_{10}$-PEG5K) after 7 days of incubation; and at the bottom are nanostructures coated with covalent polymer ($K_{10}$-PEG5K) and subsequently reduced with sodium cyanoborohydride after 7 days of incubation.

PAGE assays were further used to assess the survivability of two different barrel-like structures (60 nm and 90 nm in diameter) across multiple days. It was observed that barrels (60 nm and 90 nm) linked to (e.g., coated with) non-covalent $K_{10}$PEG5K polymer (e.g., N:P ratio of 1:1) incubated in the presence of 1 U/μL DNase I at 37° C. had a half-life for degradation of approximately 16 minutes. Meanwhile, barrels linked to (e.g., coated with) saturating amount of covalent $K_{10}$-PEG5K polymer (e.g., N:P ratio of 1:1) incubated in the presence of 0.2 U/μL DNase I had half-lives for degradation greater than 48 hours (90 nm barrel nanostructure covalently linked to (e.g., coated with) polymer) and greater than 72 hours (60 nm barrel nanostructure covalently linked to (e.g., coated with) polymer). FIG. 3A provides a graph of normalized intensities of this quantified PAGE assay for the 90 nm barrel nucleic acid nanostructures when incubated with 1 U/μL DNase over time. Increased half-lives of resistance to degradation demonstrate that nanostructures linked to (e.g., coated with) saturating levels of covalent oligolysine are significantly more resistant to nuclease degradation than nanostructures non-covalently linked to (e.g., coated with) polymers. Specifically, nanostructures covalently linked to (e.g., coated with) oligolysine were at least 180-fold more resistant to DNase I in experiments performed herein. Nanostructures covalently linked to (e.g., coated with) polymer ($K_{10}$-PEG5K) are significantly more resistant to degradation than nanostructures non-covalently linked to (e.g., coated with) polymer ($K_{10}$-PEG5K).

Further, FIG. 3B shows negative stain TEM images of nanostructures after incubation at 37° C. with 1 U/μL DNase I. As demonstrated, after 3 hours of incubation, 60 nm and 90 nm barrel nanostructures non-covalently linked to (e.g., coated with) polymer ($K_{10}$-PEG5K) have lost their structural integrity in the presence of nuclease. Meanwhile, after 7 days of incubation, 60 nm and 90 nm barrel nanostructures covalently linked to (e.g., coated with) polymer ($K_{10}$-PEG5K) (with or without subsequent reduction using sodium cyanoborohydride) retain their structural integrity in the presence of nuclease.

Example 4. Glutaraldehyde Cross-Linking of Oligolysines Coating DNA Origami Greatly Reduces Susceptibility to Nuclease Degradation Here, we show that when cross-linked with glutaraldehyde, PEGylated oligolysine-coated (XK10P) DNs are up to 2 orders of magnitude more resistant to nuclease degradation compared with coated DNs not treated with glutaraldehyde (K10P). This strategy has modest impact on cellular uptake of DNs and is nontoxic to mammalian cells, and therefore has potential for therapeutic purposes such as DN-based vaccines.

Figure 4:
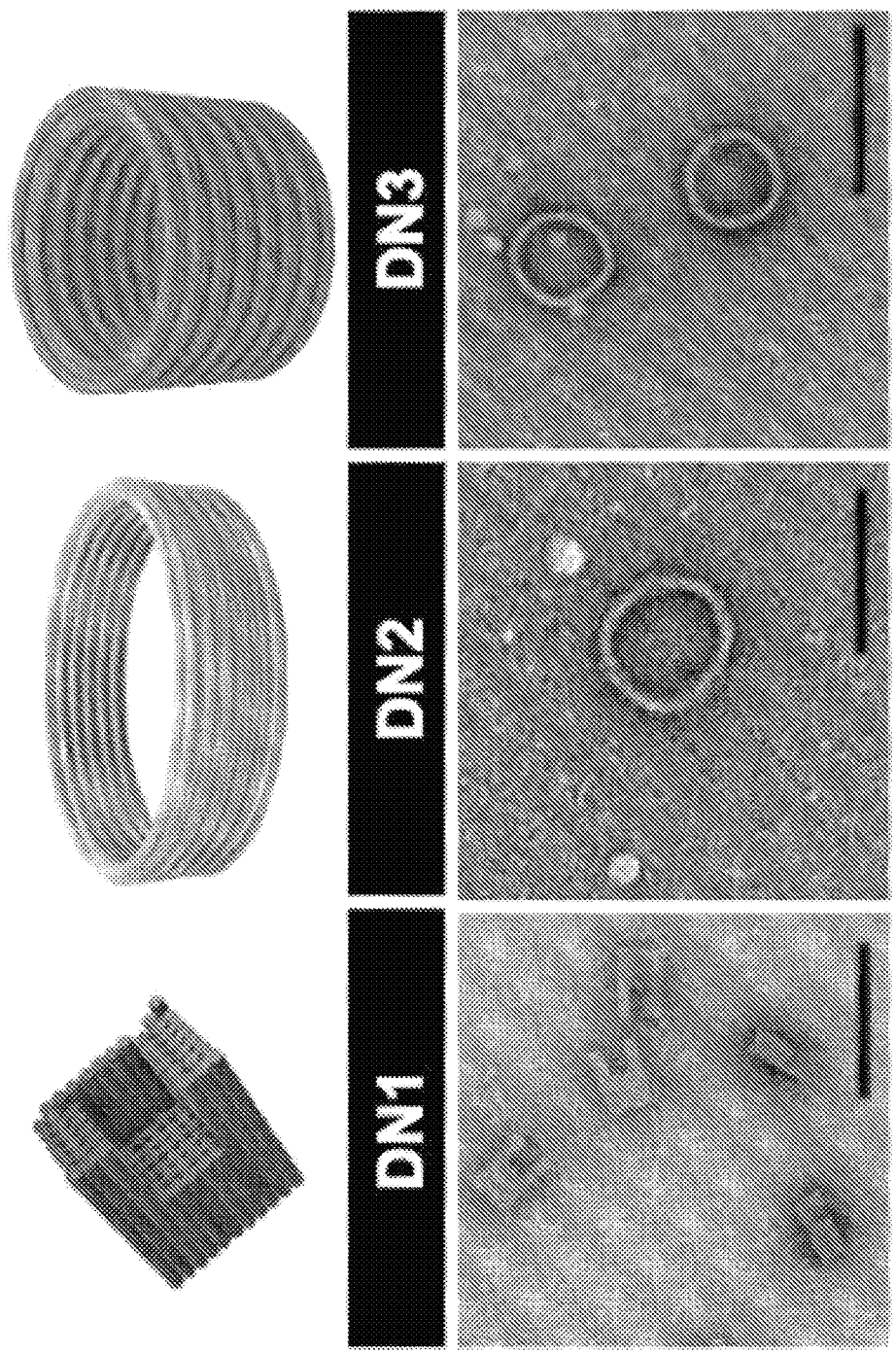
FIG. 4 shows renderings of DN1-3 and negative stain TEM images of purified structures. Scale bars, 100 nm.

We folded three structurally distinct DNs: a C-shaped DN (DN1) and two barrel-like structures with outside diameters of 90 nm (DN2) and 60 nm (DN3) (FIG. 4). DNs were designed using the software caDNAno and each folded in a one pot annealing over 18-20 h.26 Structures were purified using glycerol gradient purification and evaluated using agarose gel electrophoresis (AGE) and negative-stain transmission electron microscopy (TEM) (FIG. 4).

Figure 5:
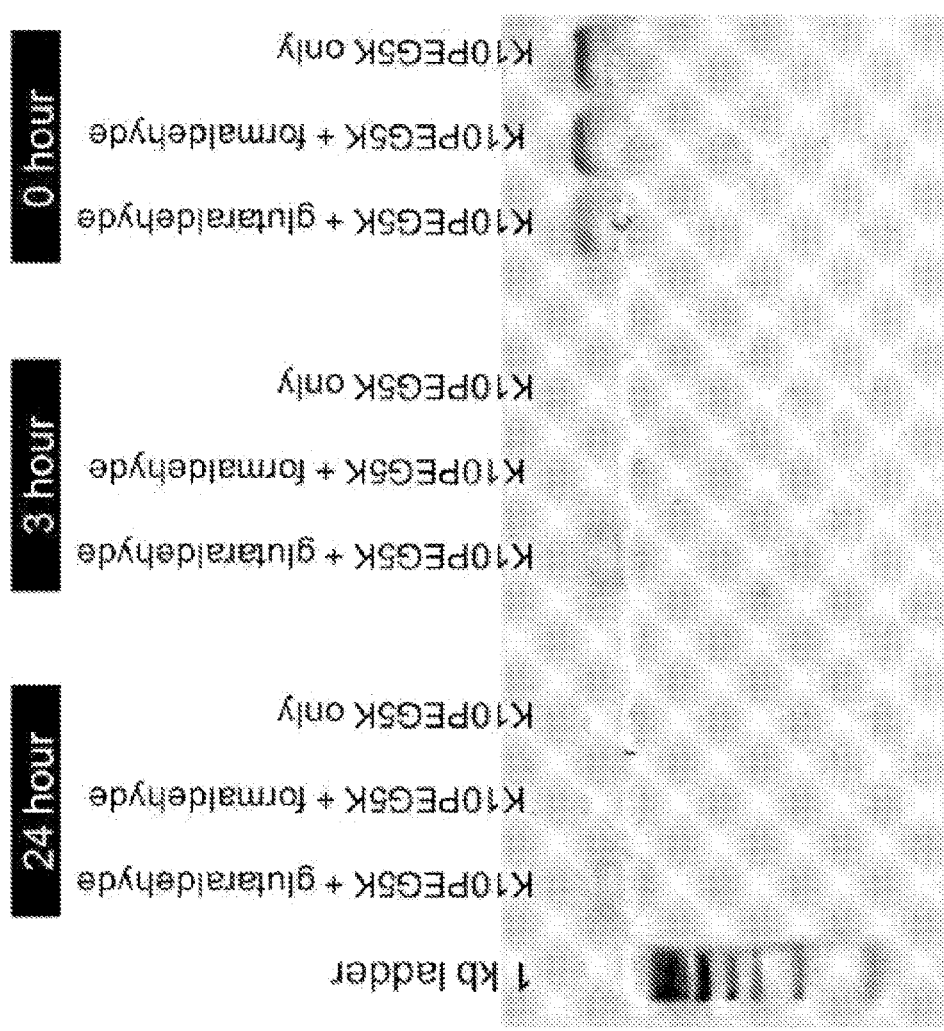
FIG. 5 shows an agarose gel electrophoresis showing complete digestion K10P-DN2 and K10P-DN2 coated with K10PEG5K and then crosslinked with formaldehyde after 3 and 24 hours of incubation with DNaseI (1 U/uL). In contrast, survival of K10P-DN2 coated with glutaldehyde was observed after 3 and 24 hours suggesting the glutaraldehyde-mediated crosslinking results in resistance to DNAseI digestion of DNs.

We first tested the ability of chemical cross-linkers to crosslink oligolysine and prevent release of staples from DNs. Among those investigated were DNA cross-linkers: cisplatin and methoxypsoralen (8-MOP) as well as formaldehyde. We also tested glutaraldehyde, which has been reported not to efficiently modify DNA at moderate temperatures. The staples band starts to disappear on denaturing polyacrylamide gel electrophoresis (PAGE) indicating either a successful cross-linking reaction between the oligolysine and DNs staples or else cross-linking of oligolysine into networks that prevent dissociation of the staple strands. To determine whether a combination of oligolysine-PEG5K coating and cross-linking could improve the survivability of DNs when challenged with nuclease degradation, we applied the oligolysine-PEG5K coating to afford K10P-DN and then added glutaraldehyde for crosslinking (XK10P-DN). Surprisingly, of the cross-linkers tested, glutaraldehyde showed the greatest ability to prevent DN denaturation and nuclease degradation (FIG. 5).

Glutaraldehyde exists in many monomeric and polymeric forms. In our experiments, monomeric glutaraldehyde forms imine bonds with primary amines in the oligolysine, and polymeric glutaraldehyde likely forms secondary amine bonds with lysines via the Michael addition mechanism to cross-link oligolysine-PEG5K molecules. We hypothesize that this covalent conjugation decreases the mobility and dissociation of the oligolysine-PEG5K coating leading to prolonged protection of DNs. This cross-linking step appears to be generalizable to any DNA origami coated with oligolysine-PEG5K, is scalable, and can be performed without specialized equipment at room temperature. Following a short incubation at room temperature, excess cross-linker was removed using desalting columns (Zeba 7k). TEM was used to verify that no structural deformation of DNs occurs (data not shown).

The degradation rate of DNs has been reported to be structure dependent. DNase I is the prominent nuclease in blood and can be used to simulate the physiological challenge posed to DNs in an in vitro test. To determine whether oligolysine-PEG5K-coated structures varied in half-life, we titrated DNase I (NEB) with various K10P-DNs and incubated reactions at 37° C. for 1.5 and 12 h. Interestingly, we found that degradation rates varied dramatically (data not shown). To test the extent to which glutaraldehyde cross-linking of PEGylated oligolysine coatings improves the survival of DNs, we challenged the origami with a highly strenuous nuclease environment of 1 U/μL DNase I. As concentrations in the blood are 340-380 U/L, our conditions represent at least a 2600-fold increase in DNase I challenge. We confirmed that application of glutaraldehyde alone to DNs does not afford any protection against DNase I (data not shown). We further confirmed that cross-linking oligolysine-coated DNs with both aged and fresh glutaraldehyde offer similar levels of protection from nuclease degradation and similar prevention of staple strand dissociation (data not shown).

Figures 6A, 6B, 6C:
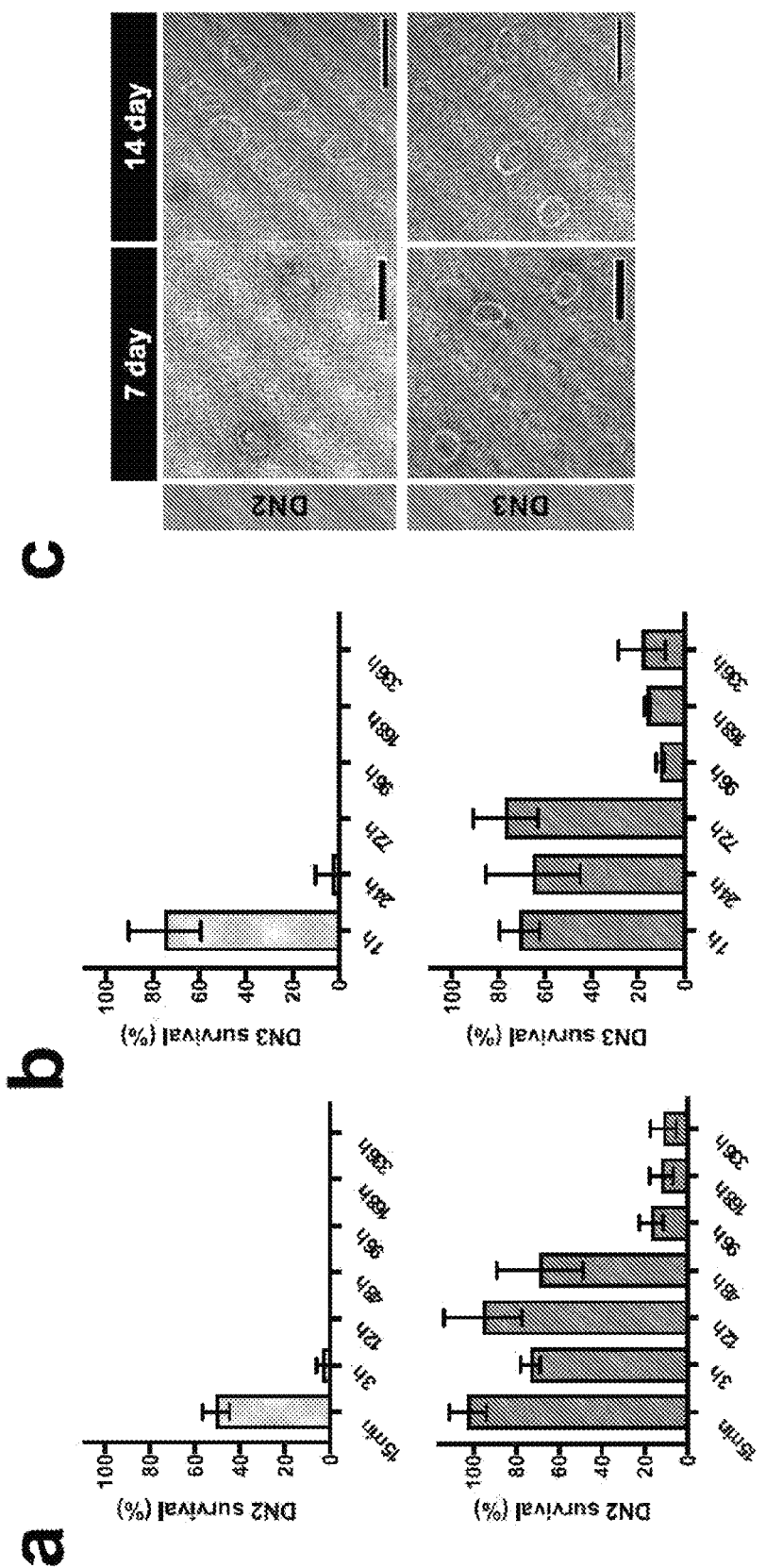
FIGS. 6A-6C show data from a time course of survival of DNs 2 and 3 in strenuous DNase I conditions. Normalized agarose gel intensity vs time using K10P-DN (top) and XK10P-DN (bottom) for (FIG. 6A) DN2 and (FIG. 6B) DN3. Error bars are ±SD, n>3.

DNs were incubated with 1 U/μL DNase I at 37° C. for different time points up to 336 h (14 days). We evaluated the quantity of surviving intact structure using AGE and TEM. Under these conditions, uncoated, i.e., bare, DN survived <1 min with no intact structure observed. We observed that XK10P-DNs show a substantially increased resistance to nuclease degradation compared to K10P-DNs (FIGS. 6A-6C). For example, K10P-DN2 showed a half-life of ~16 min with all of the structure being completely degraded by the 3 h timepoint (FIGS. 6A, 6C). However, XK10P-DN2 showed unexpected long extended half-lives, ~66 h, with approximately 12% of intact structure remaining even after 14 days of incubation under these conditions. This represents an ~250-fold increase in XK10P-DN stabilization against nucleases compared to K10PDN, based on half-life extension. We confirmed that this extended half-life could be conferred on other origami by switching to DN3 in a second set of experiments (FIGS. 6B-6C). Additionally, we verified that prolonged incubation with XK10P-DN does not affect DNase I activity (data not shown).

Under physiological conditions with 10% FBS, we expect bare DNs to have a half-life of ~5 min, and K10P-DN3 to have a half-life of approximately 36 h. We observed a 250-fold increase in stabilization compared to K10P-DN3, suggesting our strategy may enable XK10P-DNs to survive in physiological conditions with 10% FBS for over one year. However, over a long period of time, the imine bonds may hydrolyze. As a preliminary effort toward addressing this concern, we explored sodium cyanoborohydride reduction of the imine bonds formed by glutaraldehyde cross-linking of lysines. Reduction did not affect nuclease resistance in our 1 U/µL DNase I test over the course of a week (data not shown). Future experiments can explore whether reduction impacts the long-term nuclease resistance of XK10P-DNs.

A key advantage of DNs over other nanoparticles is the ability to decorate DNs precisely with diverse cargos. This is often achieved through the Watson-Crick base-pairing of a partially embedded DNA oligonucleotide from the DN (handle) with a complementary oligonucleotide (antihandle) covalently conjugated to a cargo. To ensure that XK10P-DNs could still be loaded with cargo, we evaluated handle accessibility. We found that XK10P-DN1 is able to capture cargo after a short annealing time (data not shown).

Figure 7:
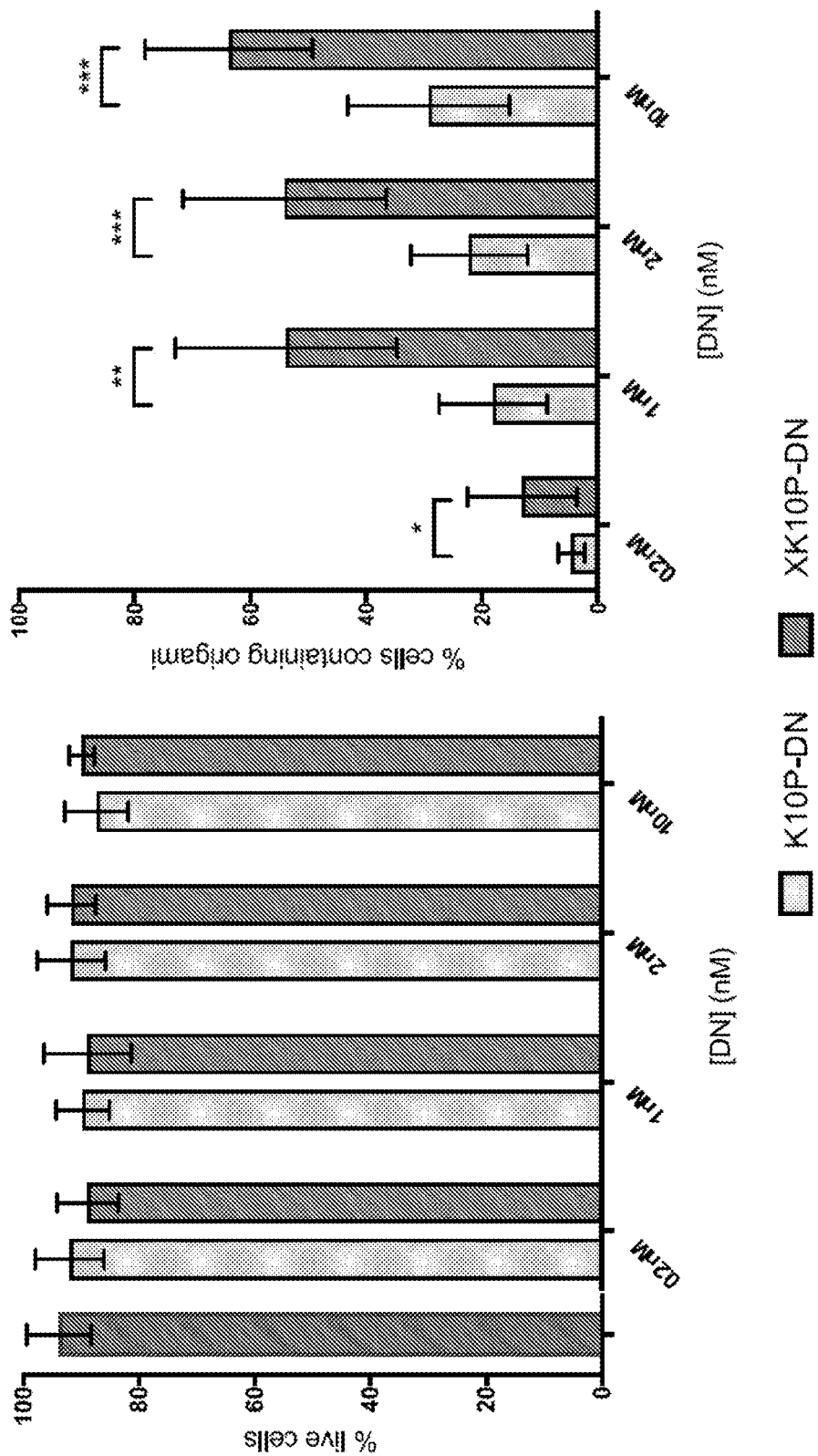
FIG. 7 shows data from studies of the interaction between XK10P-DNs and mammalian cells. Flow cytometry was used to study the impact of glutaraldehy decross-linking of DNs on (left) cell viability through labeling with membrane permeable propidium iodide and (right) cellular uptake after 24 h of HEK293T cells incubation with Cy5-fluorescent DNs. Error bars are ±SD, n≥6. *$p<0.05$; $p<0.005$; *$p<0.005$.

We next studied the interaction of our modified DNs with mammalian cells. Here, HEK293T cells diluted in standard DMEM+10% FBS (~0.7 mM $MgCl_2$) was used as a model system. Previous studies from our lab and others have shown the shape dependence of cellular uptake of DNs and K10PDNs as well as the importance of scavenger-receptor-mediated and caveolin-dependent cellular uptake for DN internalization. In this study, we focus on the stability of DNs upon internalization with the goal of improving their utility as a drug delivery system or biological tool. A necessary feature that drives DNA origami toward that goal is that the system exhibits limited toxicity. We incubated a Cy5 fluorescently labeled DN3 with mammalian cells over 8 and 24 h and at different concentrations. Using flow cytometry for quantitative assessment, we monitored cell viability through membrane permeability using propidium iodide (ThermoFisher Scientific). No significant difference in cell viability between addition of vehicle only, K10P-DN3, and XK10P-DN3 was observed (FIG. 7A).

Additionally, we studied the impact of the cross-linked coating on the cellular uptake of DNs, using DN3 as a model system. We observed greater cellular uptake with increasing DN concentration for both K10P-DNs and XK10P-DNs. XK10P-DN3 displayed, at each concentration, statistically significantly superior uptake compared to K10P-DN3 after 24 h of incubation (FIG. 4B). For example, for 10 nM DN incubation with HEK293T cells, we observed over twice the uptake for XK10P-DN3 compared to K10P-DN3 ($p<0.0005$). However, cellular uptake for K10P-DN3 and XK10PDN3 after 8 h was similar (data not shown).

A possible explanation for this discrepancy between 8 and 24 h results may be the progressive degradation of K10P-DN3 to form more amorphous structures compared to stable XK10PDN3. We observed in previous studies that compact DNs are more efficiently uptaken by HEK293 cells. Over prolonged incubations, such as 24 h incubations, this degradation could be responsible for the decreased uptake observed for K10PDNs compared to XK10P-DNs. Since higher uptake rates are typically linked to greater biological effects, cross-linking of oligolysine coatings may assist in increasing efficacy of DN-mediated drug delivery to cells.

In conclusion, we have developed an inexpensive, scalable, and generalizable method for protecting DNs in vivo that drastically increases the nuclease resistance of DNs: Once coated with an oligolysine-PEG copolymer, amines in the oligolysines can be covalently cross-linked to increase the half-life of the underlying DN under attack by nucleases.

In particular, we showed that glutaraldehyde-mediated chemical cross-linking of oligolysine-PEG5K-coated DNs increases DNs resistance to DNase I degradation under strenuous conditions up to 100,000-fold compared to bare DNs and over 250-fold compared to DNs coated with oligolysine-PEG5K but not subjected to cross-linking. We also observed a statistically significant increase in cellular uptake for XK10P-DNs compared with K10P-DNs. We believe this method is compatible with therapeutic applications since it is non-toxic and allows for the continued decoration of DNs with various surface ligands.

Fabrication DNs.

DNs were designed using caDNAno and assembled using previously published methods for folding of 3D DNA origami. Construction plans for each DN, scaffold and staple sequences are listed in SI Tables 1-3 respectively. Synthetic DNA for staples was purchased in a 100 nmole scale from IDT. Scaffolds (p7308, p8064 and p8634) were produced in-house using previously published protocols, and purified from endotoxins before use. For each shape, folding conditions used were 5 mM Tris, 1 mM EDTA (pH 8.0), 20 nM scaffold, 200 nM staple strands and 10 mM MgCl2. Folding was performed in a thermocycler with the following program per shape: for DN1, denaturing at 80° C. for 15 minutes; and then annealing at 60° C. to 25° C. at −1° C. per 31 minutes; DN2, denaturing at 80° C. for 15 minutes; and then annealing at 60° C. to 25° C. at −1° C. per 31 minutes; for DN3, denaturing at 80° C. for 15 minutes; and then annealing at 50° C. to 40° C. at −1° C. per 108 minutes. All objects were purified using glycerol gradient purification and quality of DNs was analyzed via agarose gel eletrophoresis and transmission electron microscopy.

Fluorescent Labeling of DNs.

DNs were each labelled with Cy5 fluorophores. In each case, DNA oligonucleotides were modified with a 3' amine and covalently coupled to Cy5 fluorophores via NHS ester coupling (lumiprobe.com/p/cy5-nhs-ester). In the dark, 25 uL DNA oligonucleotide (0.5 mM in ddH2O) was mixed with 12.5 uL of NHS-Cy5 (25 mM in DMSO) (25× excess) and 4.2 uL of NaHCO3 (1M, buffer at pH 8.0, (sterile filtered) was combined for a total volume of 41.7 µL. The reaction was carried out in the dark for 2 h at 25° C. Zeba size-exclusion and desalting columns (7K MWCO; Thermo Scientific, Waltham, MA) were used to remove unreacted dye through centrifugation at 1000×g for 2 min. The columns were washed with 400 µL of ddH2O three times before use according to manufacturer's protocol.

Purifying DNs.

DNs were purified using glycerol gradient purification as described by Lin et al.1 Amicon ultracentrifugation filters (50 kDa) (Milipore Sigma) were washed with (5 mM Tris, 1 mM EDTA (pH 8.0), 0.01% tween, 10 mM MgCl2) twice, before being used to concentrate DNs from folding (20 min, 4,000×g). DNs were then gently added to the top of 15-45% glycerol gradients in SW41 Ti compatible tubes. Samples were spun for 2.5 hours at 41,000 rpm at 4° C. in a Beckman Coulter preparative ultracentrifuge. Gradients were fractionated and DN monomer containing fractions were collected and cleaned from glycerol using Amicon ultracentrifugation filters.

Oligolysine-PEG5K Coating of DNs.

30 uL of 90 nM DN was mixed 1:1 (v/v) with oligolysine-PEG5K (K10-PEG5K) (Alamanda polymers) such that nitrogen in amines:phosphates in DNA ratio was 1:1, according to the published method. Samples were incubated at room temperature for 1 hour.

Glutaraldehyde Crosslinking of DNs.

60 uL of 45 nM DN was combined with 2% (v/v) glutaraldehyde (50% in H2O) (Milipore Sigma), mixed gently and incubated at room temperature over two hours. Immediately prior to use, excess small molecule was removed using Zeba size-exclusion and desalting columns (7K MWCO; Thermo Scientific, Waltham, MA). Columns were prepared as described previously. DNs were then buffer exchanged into PBS using Amicon Ultra 0.5 mL centrifugation filters (Milipore Sigma) according to manufacturer's protocol.

DNase I Degradation Assays.

DNs (10 nM final concentration) were incubated with 1.0 U/uL DNase I (NEB) with 1× DNase I buffer in sterile phosphate buffered saline (PBS) (Gibco). Samples were incubated in thermocycler at 37° C. for specific timepoints and then analyzed using agarose gel electrophoresis. Immediately prior to gel analysis, 5× oligolysine-PEG5K was added to the samples, to ensure migration of the DN band out of the well. All time points were performed in at least triplicate.

TEM Analysis.

The structural integrity of each DN was verified using negative stain transmission electron microscopy (TEM). Prior to adding the samples, grids were cleaned using plasma discharge for 30 seconds. 3.0 uL of 1 nM DN solution (1 nM) was then deposited on a carbon coated Formvar grid (Electron Microscopy Sciences). After 3 minutes, the sample was wicked from the grid by gently touching filter paper to the grid edge. A drop of uranyl formate solution (2% w/v in H2O) was then deposited onto the grid for 30 seconds, and the excess solution was wicked using filter paper. Studies were conducted using a JEOL JEM-1400 transmission electron microscope in brightfield mode at 80 kV.

Cell-Based Assays.

Cell studies were performed using Human Embryonic Kidney (HEK293) cells maintained in highglucose Dulbecco modified Eagle medium (Gibco, Gaithersburg) and 10% fetal bovine serum (FBS) (Lonza, Wakersville) with penicillin-streptomycin. For flow cytometry, HEK293 cells were seeded at a density of 250,000 cells/mL into tissue culture treated 48 well plates (BD Life Sciences) and allowed to grow for 24 hours in 200 uL of media. DNs (40 nM) were added to a final concentration of 0.2-2 nM and incubated with cells for the described amount of time. All samples were performed in triplicate.

Microscopy.

10,000 cells were seeded on tissue culture-treated 15-well ibidi slides (Cat. No. 81506) and allowed to adhere overnight. DNs were then added to a final concentration of 2 nM in 45 uL of media per well and incubated for 24 hours. After 24 hours, cells were washed with PBS with DAPI (300 nM) and incubated at room temperature for 30 min. Excess DAPI was then removed by washing with PBS and imaged on a Zeiss inverted microscope. Excitation for 640 nm for Cy5, and DAPI was 350 nm.

Flow Cytometry.

Cells incubated with DNs were washed twice with PBS (−,−) (Gibco) and digested with trypsin (0.025%) (Invitrogen) for 2 minutes at 37° C. Cells were resuspended in 250 uL of PBS and stained using Propidium Iodide (ThermoFisher Scientific). Samples were then loaded onto a flow cytometer (BD LSR Fortessa) and data was analyzed using FlowJo (Flow Cytometry Analysis Software).

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A composition comprising a deoxyribonucleic acid (DNA) nanostructure covalently linked to oligolysine-polyethylene glycol (PEG) copolymer.

2. The composition of claim 1, wherein the N:P (nitrogen in lysine to phosphorus in nucleic acid) ratio of the composition is 0.5:1 to 1:1.5.

3. The composition of claim 1, wherein the DNA nanostructure has a half-life that is at least 10000-fold greater than the half-life of an uncoated DNA nanostructure.

4. The composition of claim 1, wherein the DNA nanostructure has a half-life that is at least 150-fold or at least 180-fold greater than the half-life of a DNA nanostructure coated but not crosslinked with oligolysine-PEG copolymer.

5. The composition of claim 1, wherein the DNA nanostructure has a half-life of at least 24 hours, at least 48 hours, or at least 72 hours in a physiological buffer comprising less than 0.5 mM $Mg^{2+}$.

6. The composition of claim 1, wherein the DNA nanostructure is a three-dimensional DNA nanostructure.

7. The composition of claim 1, wherein the DNA nanostructure has a void volume of at least 25%, at least 50%, or at least 75%.

8. The composition of claim 1, wherein the oligolysine comprises 5 to 20 lysines.

9. The composition of claim 1, wherein the oligolysine comprises at least 10 lysines.

10. The composition of claim 1, wherein the PEG is PEG1K, PEG5K, PEG10K, or PEG20K.

11. The composition of claim 1 further comprising a physiological buffer and/or a buffer solution comprising less than 0.5 mM $Mg^{2+}$.

12. The composition of claim 1 further comprising DNase I.

13. The composition of claim 1, wherein the DNA nanostructure is further linked to a therapeutic, prophylactic, and/or diagnostic molecule.

14. The composition of claim 1, wherein the composition is non-toxic.

15. The composition of claim 1, wherein cellular uptake of the DNA nanostructure covalently linked to oligolysine-PEG copolymers is at least twice that of a control DNA nanostructure non-covalently linked to oligolysine-PEG copolymers.

16. A cell, optionally a mammalian cell, comprising the DNA nanostructure of claim 1.

17. A method comprising administering to a cell or a subject the composition of claim 1.

18. A method comprising covalently crosslinking a DNA nanostructure with oligolysine-PEG copolymer using glutaraldehyde to form imine bonds with primary amines in the oligolysine-PEG copolymer.

19. A method of producing a three-dimensional DNA nanostructure covalently crosslinked with oligolysine-PEG, the method comprising:
  (i) adding oligolysine-PEG to a solution comprising a three-dimensional DNA nanostructure;
  (ii) adding a crosslinking agent to the solution of (i); and
  (iii) adding a reducing agent to the solution of (ii) to produce a three-dimensional nucleic acid nanostructure coated and covalently crosslinked oligolysine-PEG.

20. The composition of claim 1, wherein the N:P (nitrogen in lysine to phosphorus in nucleic acid) ratio of the composition is 1:1.

* * * * *